(12) United States Patent
Sorscher

(10) Patent No.: US 7,473,527 B2
(45) Date of Patent: Jan. 6, 2009

(54) COMPOUNDS PROMOTING DELIVERY OF GENES

(75) Inventor: Eric J. Sorscher, Birmingham, AL (US)

(73) Assignee: The UAB Research Foundation, Birmingham, AL (US)

(*) Notice: Subject to any disclaimer, the term of this patent is extended or adjusted under 35 U.S.C. 154(b) by 416 days.

(21) Appl. No.: 10/520,377

(22) PCT Filed: Jul. 2, 2003

(86) PCT No.: PCT/US03/20732

§ 371 (c)(1), (2), (4) Date: May 19, 2005

(87) PCT Pub. No.: WO2004/005464

PCT Pub. Date: Jan. 15, 2004

(65) Prior Publication Data

US 2006/0233754 A1  Oct. 19, 2006

Related U.S. Application Data

(60) Provisional application No. 60/393,266, filed on Jul. 2, 2002.

(51) Int. Cl.
   *C12Q 1/68* (2006.01)
(52) U.S. Cl. .................. 435/6; 435/455; 424/450
(58) Field of Classification Search ................ None
   See application file for complete search history.

(56) References Cited

U.S. PATENT DOCUMENTS

| | | | |
|---|---|---|---|
| 4,226,856 A | 10/1980 | Cole | 424/177 |
| 5,264,618 A | 11/1993 | Felgner et al. | 560/224 |
| 5,538,885 A * | 7/1996 | Hollis et al. | 435/355 |
| 6,242,459 B1 | 6/2001 | Bondinell et al. | 514/297 |

OTHER PUBLICATIONS

Felgner et al., PNAS, vol. 84, 1987, pp. 7413-7417.*
Russell, David W., Alexander, Ian E., Miller, A. Dusty, "DNA synthesis and topoisomerase inhibitors increase transduction by adeno-associated virus vectors," Proc. Natl. Acad. Sci., vol. 92, p. 5719-5723, Jun. 1995.
Tobey, R., Orlicky, D., Deaven, L., Rall, L., Kissane, R., Effects of Bouvardin (NSC 259968), a Chinese Hamster Cells, Cancer Research 38, 4415-4421, Dec. 1978.
Enhanced NCI Database Browser; http://129.43.27.140/tmp/detaiUiwevB.html; NSC No. 73609; accessed Feb. 25, 2002; pp. 1-3.
Enhanced NCI Database Browser; http://129.43.27.140/tmp/detaiEQdSUB.html; NSC No. 82090; accessed Feb. 25, 2002; pp. 1-2.
Enhanced NCI Database Browser; http://129.43.27.140/tmp/detaibXta5s.html; NSC No. 101492; accessed Feb. 25, 2002; pp. 1-3.
Enhanced NCI Database Browser; http://129.43.27.140/tmp/detai9unl4t.html; NSC No. 106191; accessed Feb. 25, 2002; pp. 1-6.
Enhanced NCI Database Browser; http://129.43.27.140/tmp/detaivSwlzc.html; NSC No. 109325; accessed Feb. 25, 2002; pp. 1-3.
Enhanced NCI Database Browser; http://129.43.27.140/tmp/detaiDf55ls.html; NSC No. 128720; accessed Feb. 25, 2002; pp. 1-5.
Enhanced NCI Database Browser; http://129.43.27.140/tmp/detaitKzYNC.html; NSC No. 143491; accessed Feb. 25, 2002; pp. 1-4.
Enhanced NCI Database Browser; http://129.43.27.140/tmp/detaiyKQrrs.html; NSC No. 259968; Feb. 25, 2002; pp. 1-7.
Enhanced NCI Database Browser; http://129.43.27.140/tmp/detaiKR1owl.html; NSC No. 373989; accessed Feb. 25, 2002; pp. 1-4.
Enhanced NCI Database Browser; http://129.43.27.140/tmp/detai9AhSgp.html; NSC No. 675865; accessed Feb. 25, 2002; pp. 1-6.
Enhanced NCI Database Browser; http://129.43.27.140/tmp/detaiHskw67.html; NSC No. 108613; pp. 1-2.
Enhanced NCI Database Browser; http://129.43.27.140/tmp/detailzrYKV.html, NSC No. 102821; pp. 1-3.

* cited by examiner

*Primary Examiner*—James S Ketter
(74) *Attorney, Agent, or Firm*—Gifford, Krass, Sprinkle, Anderson & Citkowski, P.C.

(57) ABSTRACT

A process is provided for activating gene transfer in a cell by administering a gene transfer activating compound to the cell in conjunction with a gene transfer vector. A kit for activating gene transfer as well as process for identifying a compound that activates gene transfer are described. Use of a gene transfer activator compound enhances gene transfer of a given gene transfer vector.

32 Claims, 10 Drawing Sheets

HeLa/ Adenovirus/ 675865

HT29/ Adenovirus/ 675865

COMPOUNDS PROMOTING DELIVERY OF GENES

RELATED APPLICATION

This application is a U.S. national phase application under 371 of PCT Application No. PCT/US03/20732 filed Jul. 2, 2003, which claims priority of U.S. Provisional Patent Application Ser. No. 60/393,266 filed Jul. 2, 2002.

GRANT REFERENCE

The subject invention was made with government support under a grant from the National Institutes of Health, Grant Nos. NIH DK49057, NIH NIDDK 5 P30 DK54781 and NIH NCI 5 U19 CA67763. The government has certain rights in the invention.

FIELD OF THE INVENTION

The present invention generally relates to compounds promoting delivery of exogenous genes to cells. Specifically, the present invention relates to compounds which promote gene transfer via a viral vector.

BACKGROUND OF THE INVENTION

Delivery of an exogenous gene to a cell, and expressing the gene once it is delivered, is more difficult in some cell types than others. While numerous processes of enhancing exogenous gene delivery and gene expression have been developed, there is a continuing need for improved methods.

While gene transfer to cells and tissues is often complex, it is particularly difficult to transfer exogenous genes into epithelial cells (1-8). It is believed that this resistance reflects the barrier function of these tissues and failure of epithelial cell apical membranes to uptake gene transfer vectors such as adenoviral particles (4, 5). In contrast to lack of endocytic activity of epithelial apical membranes, basal membranes of epithelial cells do allow endocytosis. However, basal membranes are not accessible because of the tight junctions between cells.

Difficulty with gene transfer in epithelia using adenovirus vectors is well documented (4-6). However, such problems are not limited to adenoviral constructs and it is reasonable to imagine that the barrier function of epithelia may substantially limit transduction efficiency with vectors unrelated to adenovirus by a similar mechanism.

A number of methods have been used, both in vitro and in vivo, to overcome cellular resistance to introduction of exogenous genes. While EDTA, EGTA, other calcium chelators, and abrasion all augment gene transfer to epithelial cells, results are still less than optimal for effective in vitro studies as well as for gene therapy applications (7-8).

Gene therapy is the treatment of a pathological condition by introduction of an exogenous gene into a cell or tissue. In inherited diseases such as sickle cell anemia, $\alpha_1$ antitrypsin deficiency, phenylketonuria, hemophilia and cystic fibrosis, the goal of gene therapy is to replace a missing or defective gene in order to allow a cell or tissue to function normally. Gene therapy can also be used to eliminate abnormal cells. In pathological conditions such as cancer, inflammation and autoimmunity, this technique allows for introduction of toxins which cause death of the targeted abnormal cells.

In spite of the promise of gene therapy for management of intractable disease, inefficient transfer of genes into cells has slowed progress towards the goal of routine, reproducible treatment. The refractoriness of cells and tissues in vivo is well known. The required level of gene transfer is rarely attained in current gene therapy protocols even though only a small number of cells are required to express the therapeutic gene in order to ameliorate the pathological condition (1-3). For instance, for treatment of cystic fibrosis it has been suggested that if 5% of target epithelial cells express one Cystic Fibrosis Transmembrane Conductive Regulator (CFTR) mRNA molecule per cell, the physiologic $Cl^-$ transport defect in the airways may be overcome. Nevertheless, it has not been possible to consistently achieve even this low level of gene transfer in vivo using conventional adenoviral or other vectors.

The discovery of new means of facilitating gene transfer and enhancing exogenous gene expression would benefit both clinicians and bench scientists. Thus, if a safe transient activator of gene transfer or expression to otherwise refractory cells, tumors or tissues were identified, this agent could be administered in combination with a vector encoding a gene of choice.

SUMMARY OF THE INVENTION

A kit for activating gene transfer is provided which includes a gene transfer activating compound, packaged in a suitable container together with instructions for use to activate gene transfer.

A process for activating gene transfer of a vector to a cell is provided. An inventive process includes the steps of contacting a cell with a recombinant gene transfer vector and administering a gene transfer activating compound to the cell, such that transfer of the vector to the cell is activated.

Also described is a process for determining the efficacy of a putative gene transfer activating compound to activate gene transfer. The process includes the steps of administering a test compound to a first cell and contacting the first cell with a first amount of a recombinant vector. A further step includes contacting a second cell with a second amount of the recombinant vector wherein the second amount of the recombinant vector substantially equal to the first amount. A gene transfer indicator is assessed in the first and second cells to obtain a test measurement and a control measurement respectively. The test measurement and the control measurement are then compared to determine the efficacy of the putative gene transfer activating compound to activate gene transfer.

Further provided is a gene transfer activation composition useful in making a target more susceptible to a gene expression vector through the co-administration of a gene transfer activator compound.

DETAILED DESCRIPTION OF THE INVENTION

Figure 1:
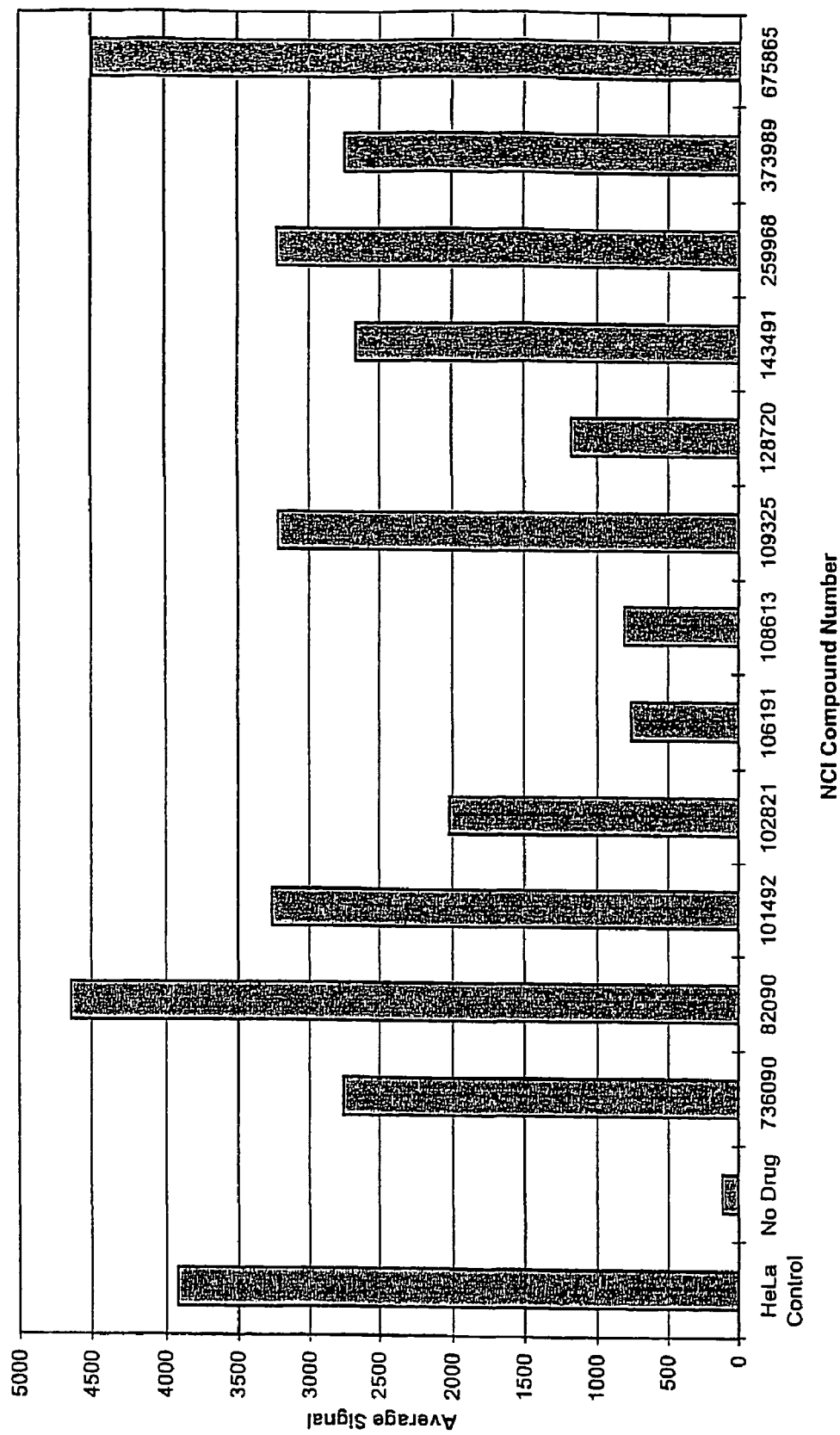
FIG. 1 is a bar graph illustrating luciferase signal in HT29 cells exposed to various gene transfer activator compounds as well as a HeLa control and a no gene transfer activator compound control.

Identifying Compounds Useful for Activating Gene Transfer

A process is provided for identifying a gene transfer activating compound. A requisite for such compounds is that a measure of gene transfer is increased in a cell exposed to a test compound compared to an unexposed cell. Numerous methods for measuring gene transfer are known in the art and some examples are described below.

A step of an inventive process provides that a first cell is contacted with a first amount of a recombinant vector. Additionally, a second cell is contacted with a second amount of the recombinant vector. Typically the first and second amounts of recombinant vector are substantially equal so that gene transfer into the first and second cells can be more easily compared. Substantially equal is intended to mean that the amounts are equal to within 10-20%.

A recombinant vector includes gene transfer vectors such as viruses, plasmids, cosmids and the like. Optionally the vector includes a nucleic acid molecule encoding a protein and a regulator or promoter sequence of said nucleic acid molecule whereby said nucleic acid molecule is transcribed and translated in the cell. In a further option, the protein encoded by the recombinant vector is a reporter gene, such as luciferase, β-galactosidase and the like.

In a further step, a putative gene transfer activating compound, or test compound, is administered to the first cell. The test compound and the vector are typically premixed prior to application to the cell, but the compound and vector may be administered separately.

In a further step of a method for determining the efficacy of a putative gene transfer activating compound, a gene transfer indicator is measured. The term "gene transfer indicator" is intended to mean any measurable molecule or effect that results from gene transfer. Gene transfer indicators include nucleic acids, proteins, reaction products and the like. Gene transfer indicators also include measurable effects on a cell attributable to gene transfer. For example, a gene transfer indicator may be cell death where the gene transfer vector introduces a molecule into a cell intended to induce an apoptotic event in the cell. The gene transfer indicator measured depends on the preference of the user, reagents available, and cell or tissue type. A gene transfer indicator is measured in a cell exposed to the test compound/vector to determine a test measurement, and a cell unexposed to the test compound in order to determine a control measurement. Gene transfer indicators include nucleic acids, proteins, reaction products and the like. Measurement of a gene transfer indicator is by standard techniques, such as polymerase chain reaction (PCR). For example, PCR may be used to detect or quantify a vector in cells exposed to vector and a test compound compared to cells exposed to a vector only. Alternatively, an expression product of a vector is measured, for example by enzyme assay, such as measurement of luciferase or β-galactosidase activity. It is appreciated that measuring a gene transfer indicator may result in a measurement that represents one or more phenomena produced by exposure of a cell to a vector and test compound. For instance, an increase in luciferase activity in a cell exposed to a test compound and a vector including luciferase encoding sequences compared to a cell exposed to vector only may represent an increased amount of vector present in the exposed cell, increased expression of luciferase by the vector, increased activity of the luciferase in a cell and the like.

In a further step of the process, the test and control measurements are compared in order to determine the efficacy of the test compound as a gene transfer activating compound. A gene transfer activating compound is identified when a test measurement differs significantly from a control measurement.

In an exemplary embodiment of a process is provided for identifying a gene transfer activating compound, confluent cells plated in multi-well cell culture units are exposed to a gene transfer vector, such as adenovirus luciferase or β-galactosidase constructs, in the presence of the test compound. The extent of gene transfer is measured by visual inspection or quantitative measurement of luciferase or β-galactosidase in the presence and absence of the test compound. Further examples are detailed below.

Compounds Identified as Gene Transfer Activators

Specific compounds identified by the assay of the present invention as gene transfer activators include those compounds designated by National Cancer Institute numbers: 73609, 82090, 101492, 102821, 106191, 108613, 109325, 128720, 143491, 259968, 373989 and 675865. Each of these numbers is commonly referred to as NSC [number], for example, NSC 73609. The term NSC [number] is derived from part of the acronym of the Cancer Chemotherapy National Service Center (CCNSC) and identifies a unique compound in an NCI database.

Compounds effective as gene transfer activators have the formula:

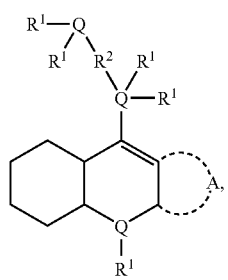

(I)

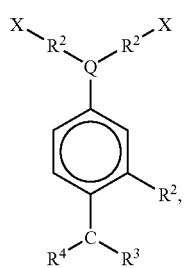

(II)

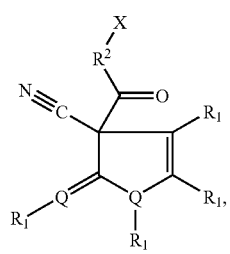

(III)

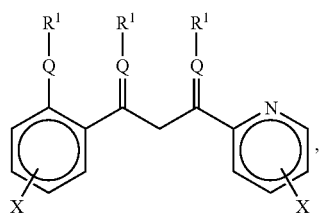

(IV)

(V)

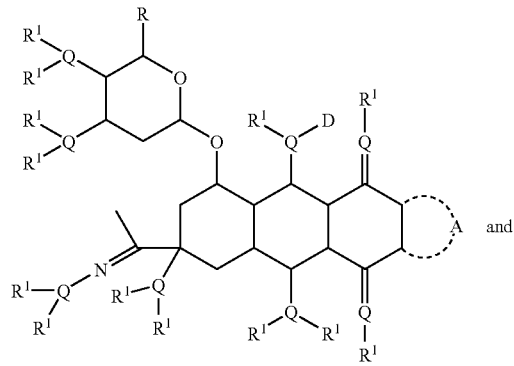

and (VI)

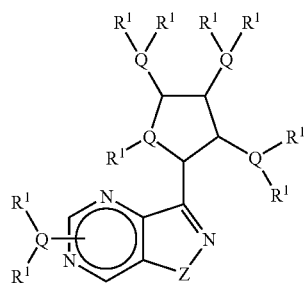

(VII)

wherein Q is nitrogen or oxygen, wherein each occurrence of $R^1$ independently is H, $CH_3$, $CH_2CH_3$ or a nullity, wherein $R_2$ is $C_1$-$C_{18}$ alleyl, $C_2$-$C_{18}$ ether, $C_2$-$C_{18}$ thioether, $C_2$-$C_{18}$ secondary or tertiary amine, wherein A is

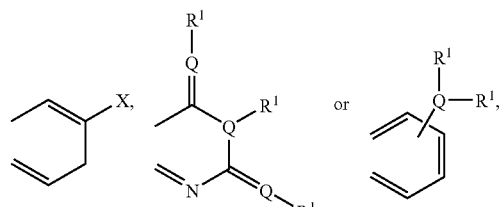

wherein $R^3$ is H, $C_1$-$C_6$ alkyl, or a heteroatom substituted $C_1$-$C_6$ alkyl where the heteroatom is oxygen, nitrogen, or sulfur, wherein $R^4$ is $C_2$-$C_6$ amide, or =N–$R^5$ where $R^5$ is $C_7$-$C_{12}$ aryloxyl, $C_1$-$C_6$ hydronyl, carbonyl, carboxyl, or acyl, imidazyl, pyrazyl, thiazyl, or oxazyl, wherein X is H, F, Cl or Br, wherein Z is oxygen or sulfur.

Recombinant Vectors

Recombinant vectors deliver an exogenous gene or other genetic material to be expressed or delivered to a cell. Genetic material illustratively includes DNA, plasmid constructs, RNA and oligonucleotides. Genetic material may include standard nucleic acid bases and/or modified forms thereof such as phosphorothioate forms and others. See, for example, Eur J Biochem. (2003) 270(8):1628-44. A recombinant vector typically includes a nucleic acid molecule encoding a protein and a promoter positioned upstream of the nucleic acid molecule. The nucleic acid is transcribed and translated in the cells to which the nucleic acid has been transferred. The recombinant vector may encode a therapeutic protein such as an IN channel cytokine, an RNA interference mediator antibody, antigen, hormone, clotting factor, receptor, enzyme, transcription factor, regulatory protein or ribozyme. Further a vector may include nucleic acid sequences that trap or sequester intracellular molecules such as regulatory proteins or detrimental mutant proteins or toxins. A vector may also encode a bacterial protein, such as *E. coli* purine nucleoside phosphorylase.

A recombinant vector may also be an oligonucleotide. Examples of this form include antisense oligonucleotides.

Among viral recombinant vectors are retroviruses (10), adenovirus (11), lentivirus (8), adeno-associated virus (13), herpes simplex virus (14) and vaccinia virus (15). A preferred embodiment of the present invention is use of compounds of the present invention to activate gene delivery using adenovirus recombinant vectors. Further preferred vectors include lentivirus and adeno-associated virus. These include both replication incompetent and permissively replicating adenovirus, lentivirus and adeno-associated virus.

A recombinant vector may also be a synthetic delivery particle such as a liposome, noisome or the like. Such delivery particles are known in the art and are constructed to deliver various materials including genetic material, proteins and drugs. See Liposome Methods and Protocols (Methods in Molecular Biology, Vol 199), S.C. Basu and M. Basu (Eds.), Humana Press, 2002.; Pharmaceutical Particulate Carriers: Therapeutic Applications (Drugs and the Pharmaceutical Sciences, Vol 61), A. Rolland (Ed.) Marcel Dekker; 1993.

Kit

A commercial kit containing a gene transfer activating compound is provided. A gene transfer activating compound included in a commercial kit activators has the formula:

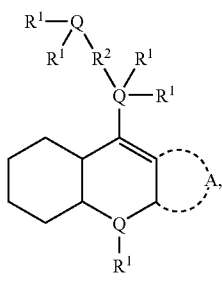

(I)

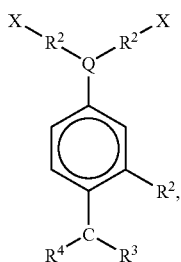

(II)

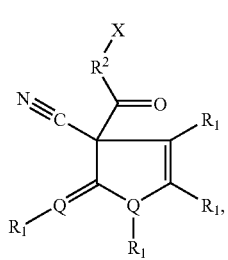

(III)

$R^2$—$AsO_3H_2$, (IV)

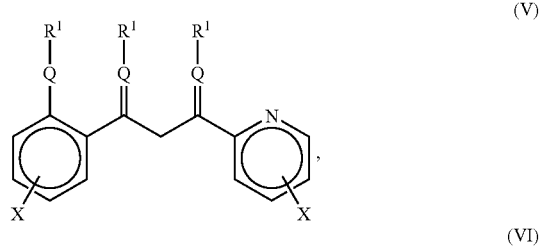

(V)

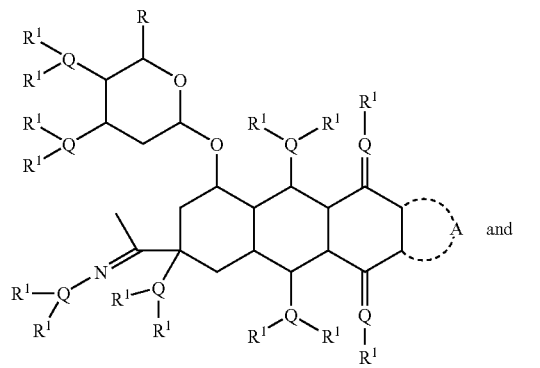

(VI)

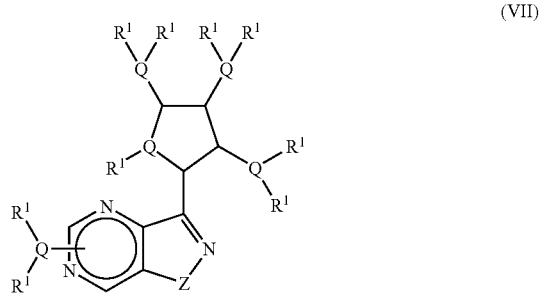

(VII)

wherein Q is nitrogen or oxygen, wherein each occurrence of $R^1$ independently is H, $CH_3$, $CH_2CH_3$ or a nullity, wherein $R^2$ is $C_1$-$C_{18}$ alleyl, $C_2$-$C_{18}$ ether, $C_2$-$C_{18}$ thioether, $C_2$-$C_{18}$ secondary or tertiary amine, wherein A is

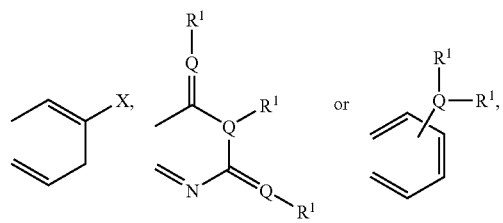

wherein $R^3$ is H, $C_1$-$C_6$ alkyl, or a heteroatom substituted $C_1$-$C_6$ alkyl where the heteroatom is oxygen, nitrogen, or sulfur, wherein $R^4$ is $C_2$-$C_6$ amide, or =N—$R^5$ where $R^5$ is $C_7$-$C_{12}$ aryloxyl, $C_1$-$C_6$ hydronyl, carbonyl, carboxyl, or acyl, imidazyl, pyrazyl, thiazyl, or oxazyl, wherein X is H, F, Cl or Br, wherein Z is oxygen or sulfur.

A gene transfer activating compound contained in the kit include those compounds designated by National Cancer Institute numbers: 73609, 82090, 101492, 102821, 106191, 108613, 109325, 128720, 143491, 259968, 373989 and 675865.

The kit optionally includes reagents, components or instructions necessary for the administration of the compounds to a cell. As a further option, an inventive kit includes a gene transfer vector. The gene transfer vector provided in the kit optionally includes a gene to be expressed in a cell.

Process For Activating Gene Transfer In A Cell

A process for activating gene transfer includes the steps of contacting the cell with a recombinant gene transfer vector and administering a gene transfer activating compound to a cell. Activation of gene transfer occurs as a result of contacting the cell with a vector and administering a gene transfer activating compound to a cell and this activation can be measured. As described above, to test for activation of gene transfer, a cell contacted by a vector and to which a gene transfer activation compound is administered is compared to a cell contacted by the vector without administration of a gene transfer activation compound. An increase in amount of vector present in a cell, an increased amount of an expressed gene, and the like, indicate activation of gene transfer.

Inventive methods, compositions and kits are used to activate gene transfer into cells including but not limited to neural cells, muscle cells, blood cells, glial cells, fibroblasts, keratinocytes, hepatocytes, epidermal cells, endothelial cells, epithelial cells and tumor cells derived from any of these. In a preferred embodiment, inventive methods, compositions and kits activate gene transfer in cells forming tight junctions.

Inventive methods, compositions and kits activate gene transfer into human cells as well as cow, horse, sheep, pig, goat, chicken, cat, dog, mouse and rat cells.

Methods of Delivering Recombinant Vectors

Methods known to those skilled in the art may be used to administer the recombinant vector in combination with a gene transfer activating compound. For example, genes may be delivered by application of a vector and gene transfer activating compound to a cell or a medium in contact with a cell. The vector may be premixed with a gene transfer activating compound and the mixture administered to a cell. Alternatively, the vector or the compound may be administered first.

Also applicable are direct injection of the recombinant vector/gene transfer activating compound combination into tissues or cells, lipid-mediated uptake, conjugation of the gene to a protein carrier, cationic liposomes, polycationic polymer-DNA complexes and biolistic methods (1, 9) and other gene transfer methods will also generally be applicable.

Administering A Gene Transfer Activating Compound To A Subject

The invention provides a method for activating gene transfer by administering at least one gene transfer activating compound to a subject with a pathological condition and administering to the subject a vector containing a nucleic acid molecule which encodes a protein and a promoter positioned upstream of the nucleic acid molecule so that the nucleic acid molecule is transcribed and translated in the target cells of the subject. Thus, in a cell or tissue lacking a normal protein, the invention has utility in providing the cell or tissue with genetic material to synthesize the needed protein.

The compounds and methods of the present invention are used to activate transfer of genetic material to subjects illustratively including human, cow, horse, sheep, pig, goat, chicken, cat, dog, mouse and rat.

The present invention provides compounds and methods useful in treatment of pathological conditions or diseases where it is desirable to introduce an exogenous protein or genetic material into the target cells or tissues of a subject. Illustrative examples of such target cells or tissues include those of the skin, nervous system, cardiovascular system, immune system, reproductive system, musculoskeletal system, lymphatic system, alimentary system, excretory system, endocrine system, hormone system and blood circulatory system. In a preferred embodiment, the present invention activates gene transfer into an epithelial cell.

An example of the general type of pathological conditions or diseases that could be treated using the compounds and methods of the present invention is those in which at least one normal protein is lacking, either missing or produced at reduced levels. Such conditions or diseases illustratively include galactosemia, phenylketonuria, Duchenne muscular dystrophy, Lesh-Nyhan syndrome, severe combined immunodeficiency syndrome, thalassemia, sickle cell anemia, cystic fibrosis, $\alpha_1$ antitrypsin deficiency, cancer, lysosomal storage disorders, porphyria and hemophilia.

In addition, the compounds and methods of the present invention are useful in treatment of conditions or diseases where it is desirable to introduce an exogenous protein which functions to reduce levels of a mutant protein. An example of the general type of pathological condition or disease where this applies is a mutation in one allele of a protein which results in a dominant phenotype which has negative effects on the cell, tissue or organism. In such a case, levels of the mutant protein may be reduced, leaving the normal protein produced by the non-mutant allele to fulfill its function. Specific elimination of an undesirable protein may be achieved by expression of specific ribozymes (16).

In addition, the compounds and methods of the present invention are useful in treatment of conditions or diseases where it is desirable to introduce an exogenous protein or genetic material which is not a normal component of the target cell or tissue. Examples include methods for treatment of growth of abnormal cells, such as cancer cells, and treatment of viral infection. In certain of these cases, a gene is transferred to target cells to produce an enzyme which acts on co-administered agents to produce toxins that destroy the target cell.

The term "active amount of a gene transfer activating compound" as used herein is intended to mean an amount of a gene transfer activating compound that, when administered to a cell in combination with a recombinant vector, simultaneously or not, ameliorates a symptom of a disease, disorder, or condition.

The term "active amount of a recombinant vector" as used herein is intended to mean an amount of a recombinant vector that, when administered to a cell in combination with a gene transfer activating compound, simultaneously or not, ameliorates a symptom of a disease, disorder, or condition.

The term "abnormal cell" as used herein is intended to mean a cell which is anomalous in any of a number of ways including but not limited to: dividing in an uncontrolled manner, having chromosomal abnormalities, having atypical functional properties such as, uncontrolled release or uptake of cellular products, loss of usual contact inhibition, and unusual migratory properties. In addition, abnormal cells might be characterized by failure to mature along normal functional lines, by widely varying in size compared to a typical cell of its type and by loss of usual orientation of the cells to one another.

The term "pathogenic viral infection" as used herein is intended to mean infection by a virus causing disease or pathological effects and is distinguished from therapeutic viral infection.

The term "mutant" as used herein is intended to mean a change in a gene which has deleterious effects on the cell or organism in which the mutation occurred.

Methods of Treatment

The method of treatment basically consists of providing to cells the gene to be transferred and exposing the cells to at least one gene transfer activating compound. It will be apparent to one skilled in the art that multiple genes may be transferred. For example, more than one adenovirus construct or plasmid may be delivered to a cell or tissue. The gene to be transferred can be delivered directly to the targeted cells or tissue or administered systemically. In the latter case, the gene is delivered in combination with a targeting means, such as through the selection of a particular viral vector or delivery formulation. The gene transfer activating compound can also be administered directly to targeted cells or tissues, or systemically. Cells can be treated in vivo, within the patient to be treated, or treated ex vivo, then injected into the patient. Further, cells or tissue may be treated and maintained in vitro.

In some applications of a process provided by the present invention, cells that receive the recombinant vector are administered to the subject. A preferred embodiment of this process involves the ex vivo transfer of the gene to be expressed by incubation of the cells with the gene transfer construct and the gene transfer activating compound outside the body of the subject. The cells that receive the gene are introduced back into the subject where they express the therapeutic protein.

The route of gene transfer activating compound administration to a subject is oral, rectal, intraventricular, intracranial, intratumoral, intrathecal, intracisternal, intravaginal, parenteral, intravenous, intramuscular, subcutaneous, local, intraperitoneal, transdermal, by inhalation or as a buccal or nasal spray. The exact amount of gene transfer activating compounds required will vary from subject to subject, depending on the age, weight and general condition of the subject, the severity of the disease that is being treated, the location and size of the tumor, the particular compounds used, the mode of administration, and the like. An appropriate amount may be determined by one of ordinary skill in the art using only routine experimentation given the teachings herein.

The route of delivery of a pharmaceutically active amount of recombinant vector is oral, rectal, intraventricular, intracranial, intratumoral, intrathecal, intracisternal, intravaginal, parenteral, intravenous, intramuscular, subcutaneous, local, intraperitoneal, transdermal, by inhalation or as a buccal or nasal spray. The exact amount of recombinant vector required as a pharmaceutically active amount will vary from subject to subject, depending on the age, weight and general condition of the subject, the severity of the disease that is being treated, the location and size of the tumor, the particular compounds used, the mode of delivery, and the like. An appropriate amount may be determined by one of ordinary skill in the art using only routine experimentation given the teachings herein.

Formulation

Depending on the intended mode of administration or delivery, the gene transfer activating compounds and recombinant vector can be in administered to a subject or cell as compositions in the form of solid, semi-solid or liquid dosage forms as desired in a particular application. For example, the gene transfer activating compounds and recombinant vector may be each individually formulated as powders, liquids, or suspensions, preferably in unit dosage form suitable for single administration of a precise dosage. In addition, formulations as pills, capsules, suppositories, or tablets may be appropriated for administration to a subject.

The compositions will include an effective amount of the selected gene transfer activating compound and/or vector in combination with a biologically acceptable carrier and, in addition, may include other medicinal agents, pharmaceutical agents, carriers, or diluents. By "biologically acceptable" is meant a material that is not biologically or otherwise undesirable, which can be administered to a subject along with the selected gene transfer activating compounds without causing significant undesirable biological effects or interacting in a deleterious manner with any of the other components of the pharmaceutical composition in which it is contained.

Compositions may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols, suitable mixtures thereof, vegetable oils and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption can be brought about by the use of agents delaying absorption, for example, aluminum monostearate and gelatin.

Solid dosage forms include capsules, tablets, pills, powders, and granules. In such solid dosage forms, the active compound is admixed with at least one inert customary excipient such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner.

Examples of embedding compositions which can be used are polymeric substances and waxes. The active compounds can also be in micro-encapsulated form, if appropriate, with one or more of the above-mentioned excipients.

Liquid forms include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, ethyl carbonate, ethyl acetate, benzyl alcohol, benzyl benzoate, propyleneglycol, 1,3-butyleneglycol, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the compositions can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administration to a subject are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention to a subject include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate and laurylsulphonate salts, and the like. These may include cations based on the alkali and alkaline earth metals, such as sodium, lithium, potassium, calcium, magnesium, and the like, as well as non-toxic ammonium, quaternary ammonium and amine cations including, but not limited to ammonium, tetramethylammonium, tetraethylammonium, methylamine, dimethylamine, trimethylamine, triethylamine, ethylamine, and the like. See, for example, S. M. Berge, et al., "Pharmaceutical Salts," *J. Pharm. Sci.*, 1977; 66:1-19.

Examples of pharmaceutically acceptable, non-toxic esters of the compounds of this invention include $C_1$-$C_6$ alkyl esters wherein the alkyl group is a straight or branched chain. Acceptable esters also include $C_5$-$C_7$ cycloalkyl esters as well as arylalkyl esters such as, but not limited to benzyl. $C_1$-$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$-$C_6$ alkyl amines and secondary $C_1$-$C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1$-$C_3$ alkyl primary amines, and $C_1$-$C_2$ dialkyl secondary amines are preferred. Amides of the compounds of the invention may be prepared according to conventional methods.

The term "prodrug" refers to compounds that are rapidly transformed in vivo to yield the parent compound of the above formula, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention can exist in different stereoisomeric forms by virtue of the presence of asymmetric centers in the compounds. It is contemplated that all stereoisomeric forms of the compounds, as well as mixtures thereof including racemic mixtures, form part of this invention.

The compounds of the present invention are administered to a subject at various dosage levels. The dosage depends on a number of factors illustratively including the size and age of the subject, the severity of the condition being treated, and the pharmacological activity of the compound being used. The determination of optimum dosages for a particular patient is well known to those skilled in the art.

In addition, it is intended that the present invention cover compounds made either using standard organic synthetic techniques, including combinatorial chemistry or by biological methods, such as through metabolism.

Gene Transfer Activating Composition

An inventive gene transfer activating composition includes a gene transfer vector as described herein and a gene transfer activating compound as described herein.

EXAMPLES

The following examples are given for the purpose of illustrating various embodiments of the invention and are not meant to limit the present invention in any fashion.

Example 1

HT29 cells are grown in 96-well plates. The cells are seeded at near confluency, about 300,000 cells per well, and infected with adenovirus 3-4 days later. At confluency on filters these tumor cells establish a resistance of 200-1000 $\Omega \cdot cm^2$ and exhibit vectoral chloride transport, two useful endpoints in evaluating viability. For screening purposes, cells are grown on plastic. Confluent monolayers under these conditions exhibit marked resistance to adenovirus transduction. The activity of candidate compounds may be also confirmed using polarized monolayers grown on filters. Once confluent, HT29 cells are very difficult to transduce with adenoviral constructs. Fewer than 1 in 100 cells express adenoviral transgenes at multiplicity of infection (MOI) of approximately 50. A replication deficient adenovirus encoding firefly luciferase or the EGFP at an MOI of 50 for each well of cells in low serum medium is applied for 4 hours at 37° C. Confluent HeLa cells are used as a positive control. A set of cells is incubated with virus but no gene transfer activating compound as a negative control. Test drugs are incubated along with the virus. Forty-eight hours later, the cells are assayed for luciferase by standard techniques. Luciferase is assayed using a commercially available kit (Promega) which allows quantitative measurements of adenoviral gene transfer. The results are shown in FIG. 1.

Example 2

HT29 or HeLa cells are grown in 96-well plates. The HT29 cells are seeded at near confluency, about 300,000 cells per well, and infected with adenovirus 3-4 days later. Confluent HeLa cells are used as a positive control. Confluent monolayers under these conditions exhibit marked resistance to adenovirus entry. A replication deficient adenovirus encoding the EGFP gene is applied at an MOI of 0.1-10 to wells of cells in low serum medium for 4 hours at 37° C. Gene transfer activating compounds are incubated along with the virus at concentrations of 100 micromolar. Cells are visualized with a fluorescent microscope where green fluorescence indicates EGFP expression. A set of cells is incubated with virus but no gene transfer activating compound. NSC compound 675865 shows activation of adenovirus gene transfer at 100 micromolar concentration in HT29 cells.

Example 3

The procedure of Example 1 is repeated in turn with 1032 compounds obtained from the NSC library. NSC compounds 73609, 82090, 101492, 102821, 106191, 108613, 109325, 128720, 143491, 259968, 373989 and 675865 are observed to show activation of adenovirus gene transfer at 100 micromolar concentrations in HT29 cells.

Example 4

Calu3 epithelial cells are grown in 96-well plates. The cells are seeded at near confluency, about 300,000 cells per well, and infected with adenovirus 3-4 days later. A replication deficient adenovirus encoding luciferase is applied at an MOI of 5 or 10 to wells of cells in low serum medium for 4 hours at 37° C. Each of the numerically identified NSC compounds of FIG. 1 individually is incubated along with the virus at a concentration of 100 micromolar. A set of cells is incubated with virus but no gene transfer activating compound. Forty-eight hours later, the cells are assayed for luciferase by standard techniques. Luciferase assay of cells incubated in the presence of the activating NSC compound show luminometric counts greater than that of cells incubated absent the activating compound.

Example 5

HT29 cells are grown in 96-well plates. The cells are seeded at near confluency, about 300,000 cells per well, and infected with adenovirus 3-4 days later. Confluent monolayers under these conditions exhibit marked resistance to adenovirus transduction. A replication deficient adenovirus encoding EGFP is applied at an MOI of 10 to wells of cells in low serum medium for 4 hours at 37° C. Numerically identified NSC compounds of FIG. 1 individually are incubated along with the virus at a concentration of 100 micromolar. A second set of cells is incubated with virus but no gene transfer activating compound and a third set of cells is incubated with virus and 5 millimolar EGTA. Forty-eight hours later, the cells are assayed for green fluorescein by standard techniques.

Example 6

Prostate or colon tumors are established in suitable hosts and *E. coli* purine nucleoside phosphorylase (PNP) activity assayed in the presence or absence of adenovirus encoding PNP. Approximately $2-3 \times 10^9$ adenoviral particles are administered per tumor in the presence of 100 micromolar—1 milimolar of each of the numerically identified NSC compounds of FIG. 1 individually or in the absence of the compound, as a control. Transgene activity is also assayed in livers. Further details of the method are described in the literature (2). PNP activity in tumors exposed to an inventive compound are higher than those observed in the controls.

Example 7

Numerically identified NSC compounds of FIG. 1 individually are assayed for effects on cell proliferation using HT29 and HeLa cells cultured at medium confluency. Each compound is added to achieve a final concentration of 10 micromolar or 100 micromolar. Measurements of cell proliferation are made according to the manufacturer's protocol using the Cytotox 96 non-radioactive assay which is commercially available from Promega Corp., Madison, Wis.

Example 8

Compound 675865 is tested extensively over a wide concentration range, with various cell types, and with various gene transfer vectors at differing MOIs.

Figure 2A:
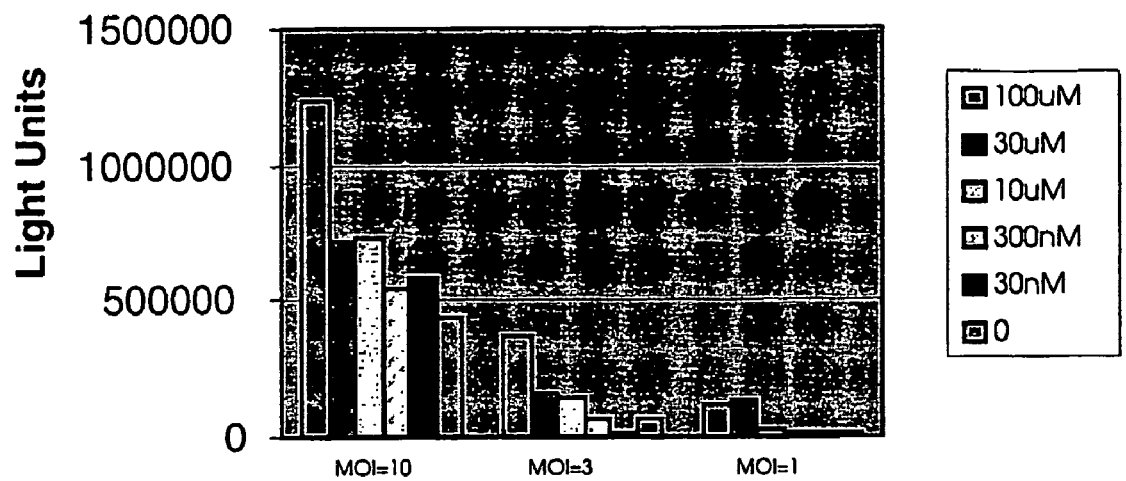
FIG. 2A is a bar graph illustrating luciferase signal in HeLa cells exposed to various concentrations of compound 675865 at differing multiplicities of infection (MOI) of an adenovirus vector expressing luciferase.
Figure 2B:
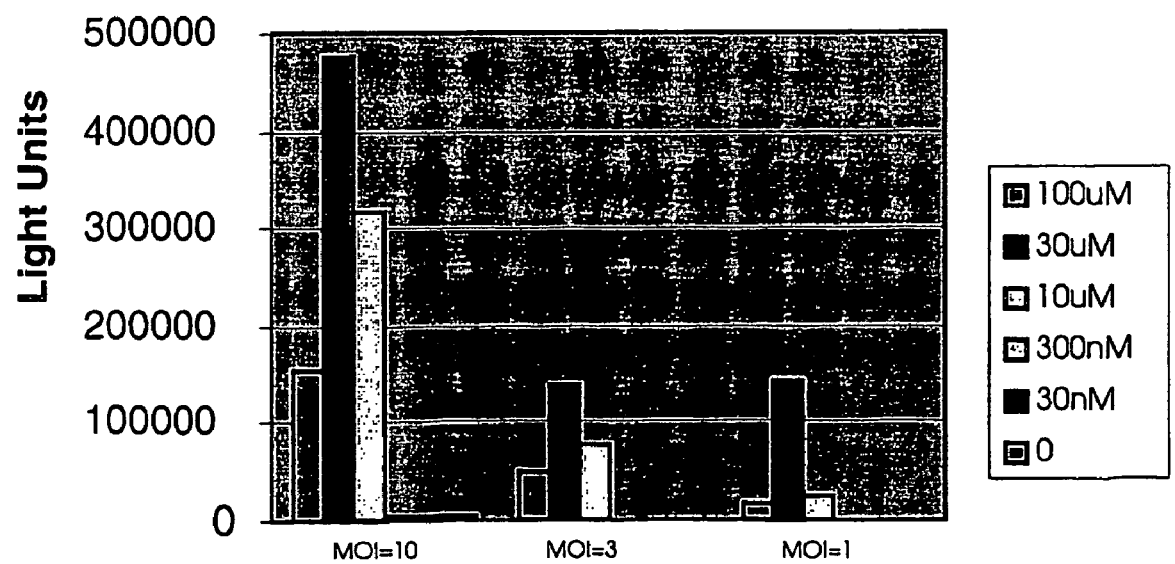
FIG. 2B is a bar graph illustrating luciferase signal in HT29 cells exposed to various concentrations of compound 675865 at differing MOI of an adenovirus vector expressing luciferase.
Figure 3A:
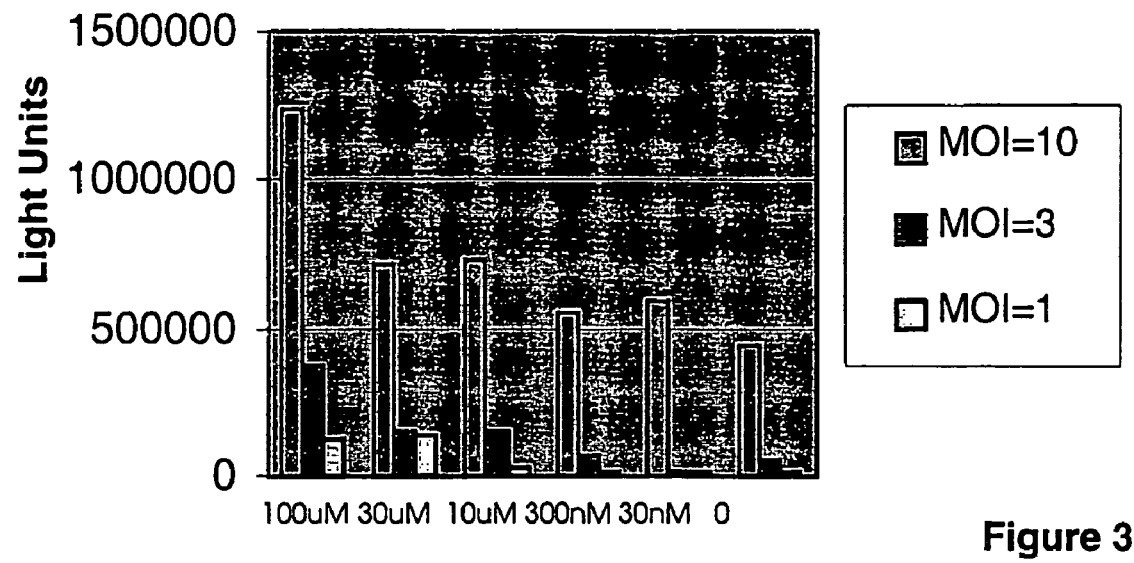
FIG. 3A is a bar graph illustrating luciferase signal in HeLa cells 5 exposed to various concentrations of compound 675865 at differing MOI of an adenovirus vector expressing luciferase.
Figure 3B:
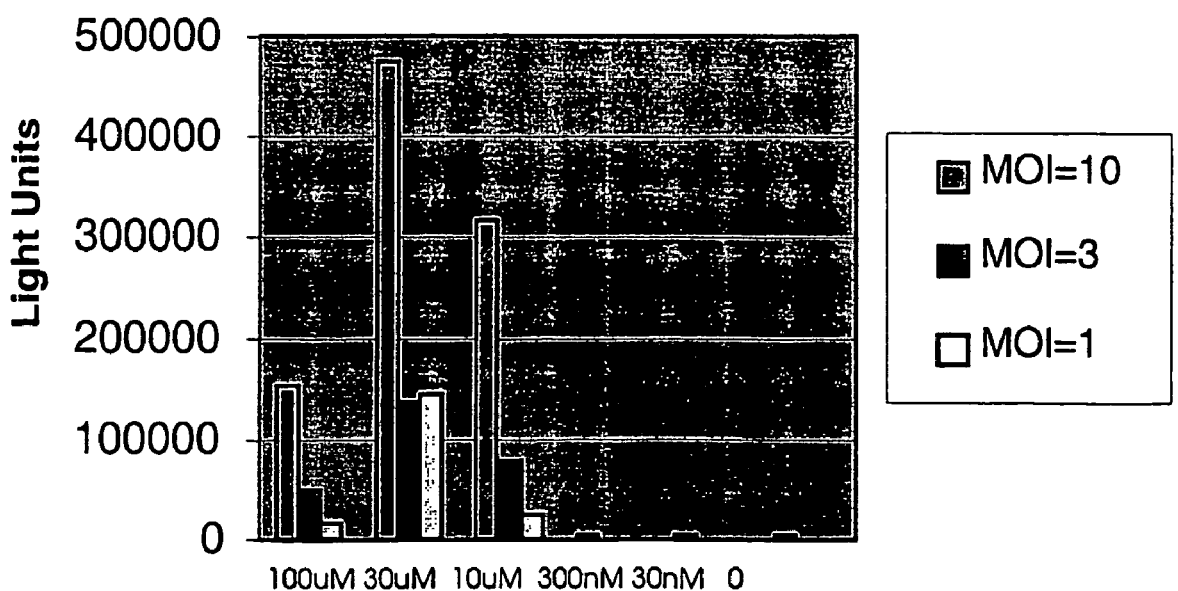
FIG. 3B is a bar graph illustrating luciferase signal in HT29 cells exposed to various concentrations of compound 675865 at differing MOI of an adenovirus vector expressing luciferase.

FIGS. 2A and 2B show a comparison of luciferase expression (y-axis, light units) vs. MOI (x-axis) in HeLa and HT29 cells infected with adenovirus under various conditions. For these studies, cells are grown in 96-well plates. The HT29 cells are seeded at near confluency, about 300,000 cells per well, and infected with adenovirus 3-4 days later. The cells are infected with luciferase-expressing, replication-deficient adenovirus at MOIs of 1, 3 or 10 by applying the virus to wells of cells in low serum medium for 4 hours at 37° C. In addition, the cells are incubated with gene transfer activating compound 675865 at a concentration of 30 nM, 300 nM, 10 uM, 30 uM or 100 uM along with the virus. A control set of cells is incubated with virus at MOIs of 1, 3 or 10, but no gene transfer activating compound is included. Forty-eight hours later, the cells are assayed for luciferase activity by standard techniques. NSC compound 675865 shows activation of adenovirus gene transfer even in HT29 cells. FIGS. 3A and 3B present data from these experiments in which luciferase expression (y-axis, light units) is plotted vs. compound 675865 concentration (x-axis).

Example 9

Figure 4A:
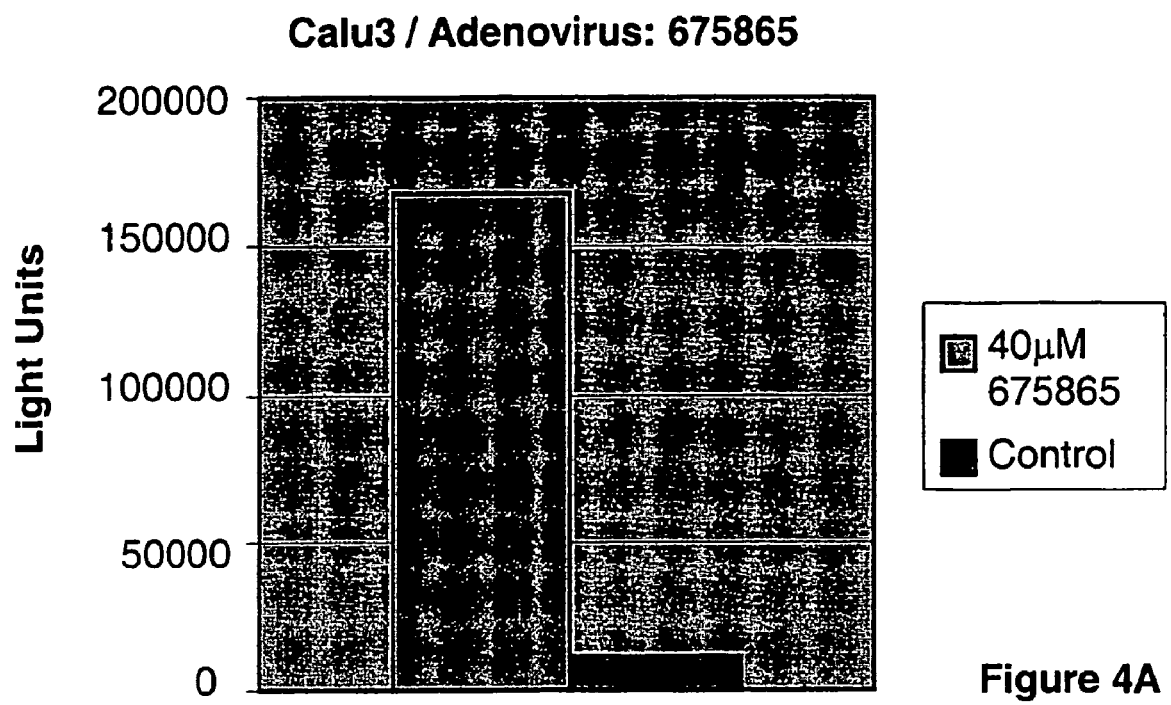
FIG. 4A is a bar graph illustrating luciferase signal in Calu3 cells exposed to 40 micromolar of compound 675865 at 10 MOI of an adenovirus vector expressing luciferase compared with luciferase expression in cells exposed to virus but no compound 675865.

Lung epithelial cells which form tight junctions in vitro, Calu3, are grown on filters (Corning Costar Transwell®— polyester—pore size 0.4 μm) or plastic well allowing apical and basolateral specialization to occur. As shown in FIG. 4A, increased luciferase activity is detected in Calu3 cells infected with luciferase expressing adenovirus in the presence of 40 μm compound 675865.

Example 10

Figure 4B:
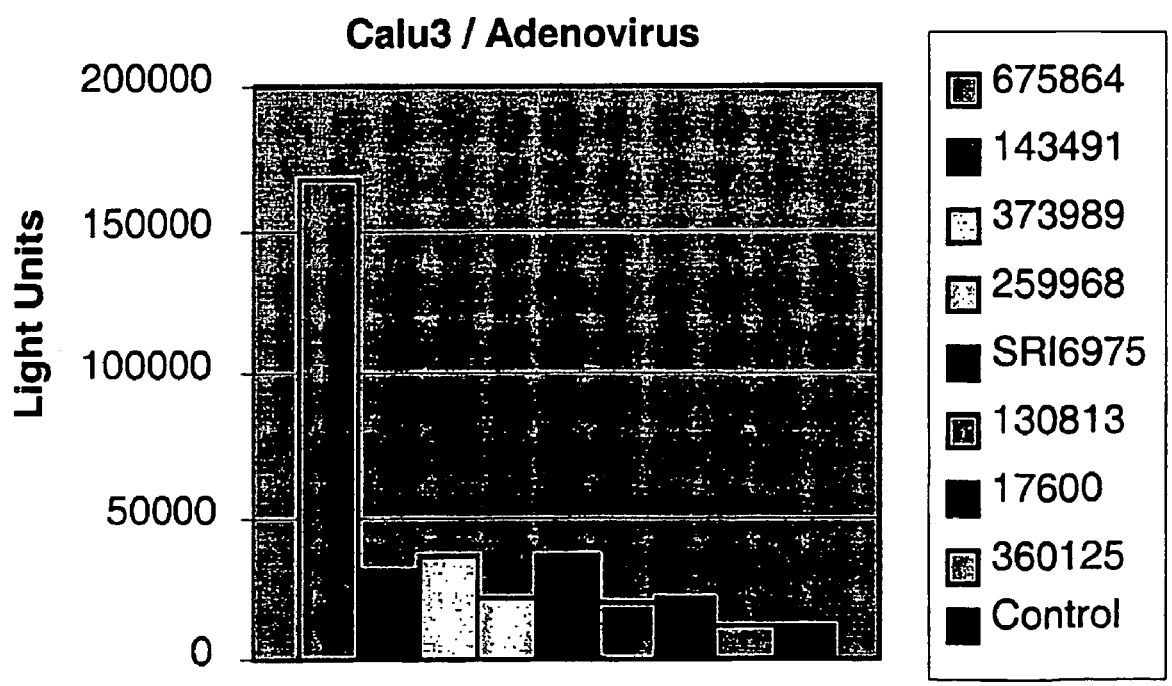
FIG. 4B is a bar graph illustrating luciferase signal in Calu3 cells exposed to 40 micromolar concentration of various compounds at 10 MOI of an adenovirus vector expressing luciferase compared with luciferase expression in cells exposed to virus but no activating compound.

Calu3 cells grown as described in Example 9 are incubated with adenovirus at 10 MOI and various compounds at a concentration of 40 micromolar. FIG. 4B indicates luciferase activity measured under these conditions.

Example 11

Figure 5A:
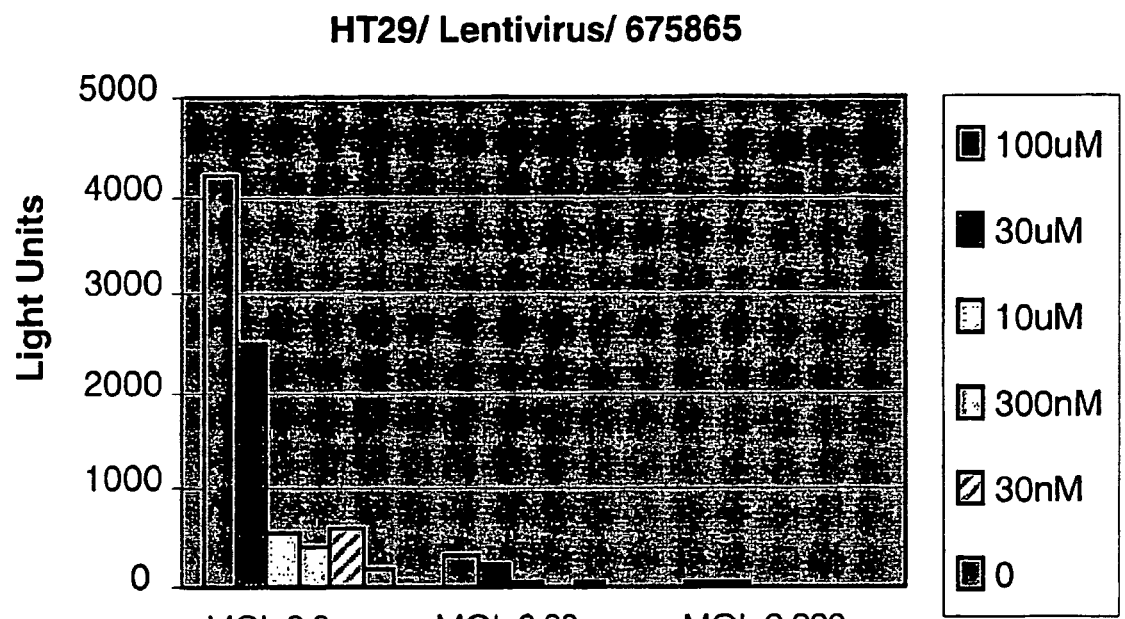
FIG. 5A is a bar graph illustrating luciferase signal in HT29 cells exposed to various concentrations of compound 675865 at differing MOI of a lentivirus vector expressing luciferase.

FIG. 5A show a comparison of luciferase expression (y-axis, light units) vs. MOI (x-axis) in HT29 cells infected with lentivirus under various conditions. For these studies, cells are grown in 96-well plates as described in Example 8. The HT29 cells are seeded at near confluency, about 300,000 cells per well, and infected with a lentivirus vector expressing luciferase 3-4 days later. The cells are infected with lentivirus at MOIs of 0.002, 0.02 or 0.2 by applying the virus to wells of cells in low serum medium for 4 hours at 37° C. In addition, the cells are incubated with gene transfer activating compound 675865 at a concentration of 30 nM, 300 nM, 10 uM, 30 uM or 100 uM along with the virus. A control set of cells is incubated with virus at MOIs of 0.002, 0.02 or 0.2 but no gene transfer activating compound is included. Forty-eight hours later, the cells are assayed for luciferase activity by standard techniques.

Figure 5B:
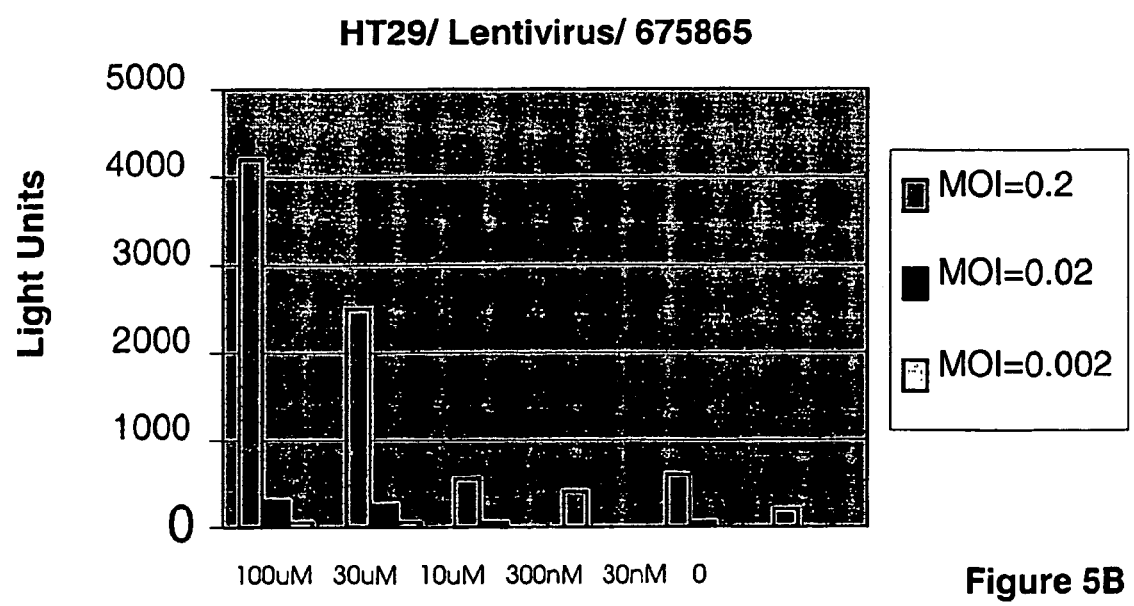
FIG. 5B is a bar graph illustrating luciferase signal in HT29 cells exposed to various concentrations of compound 675865 at differing MOI of a lentivirus vector expressing luciferase.

Results show enhancement of luciferase activity when compound 675865 is used. FIG. 5B present data from these experiments in which luciferase expression (y-axis, light units) is plotted vs. compound 675865 concentration (x-axis).

Example 12

Compound 143491 is tested extensively over a wide concentration range, with various cell types, and with various gene transfer vectors at differing MOIs.

Figure 6A:
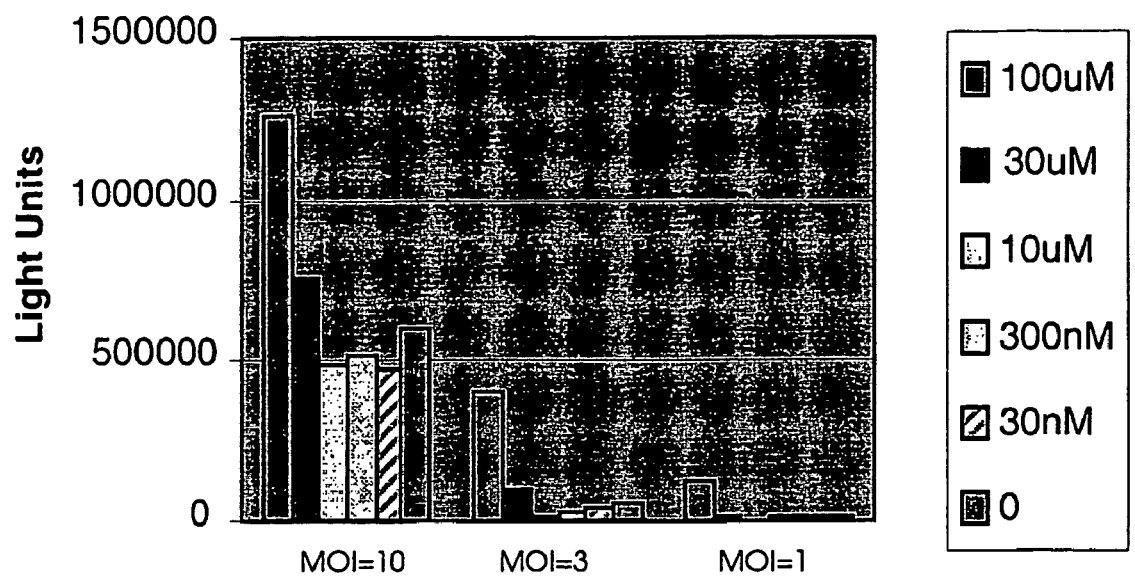
FIG. 6A is a bar graph illustrating luciferase signal in HeLa cells exposed to various concentrations of compound 143491 at differing MOI of an adenovirus vector expressing luciferase.
Figure 6B:
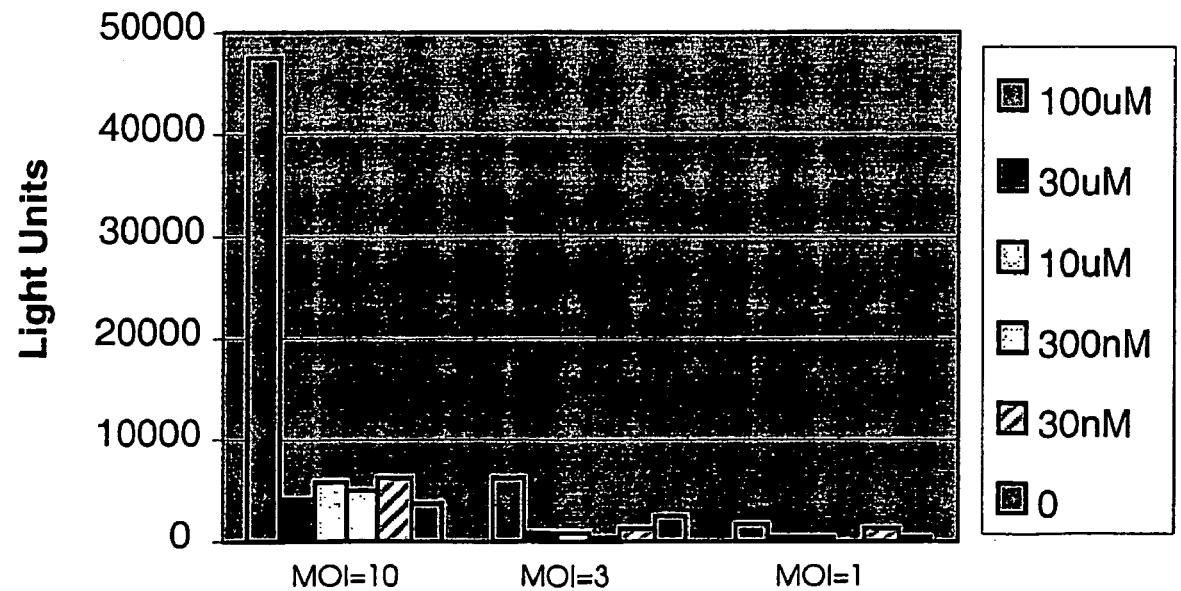
FIG. 6B is a bar graph illustrating luciferase signal in HT29 cells exposed to various concentrations of compound 143491 at differing MOI of an adenovirus vector expressing luciferase.
Figure 7A:
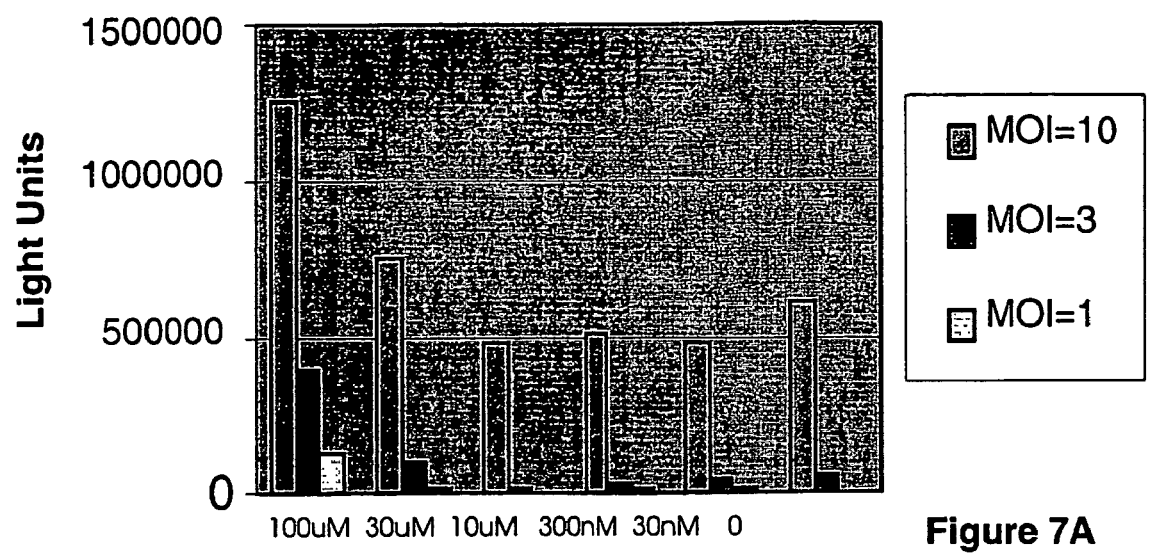
FIG. 7A is a bar graph illustrating luciferase signal in HeLa cells exposed to various concentrations of compound 143491 at differing MOI of an adenovirus vector expressing luciferase.
Figure 7B:
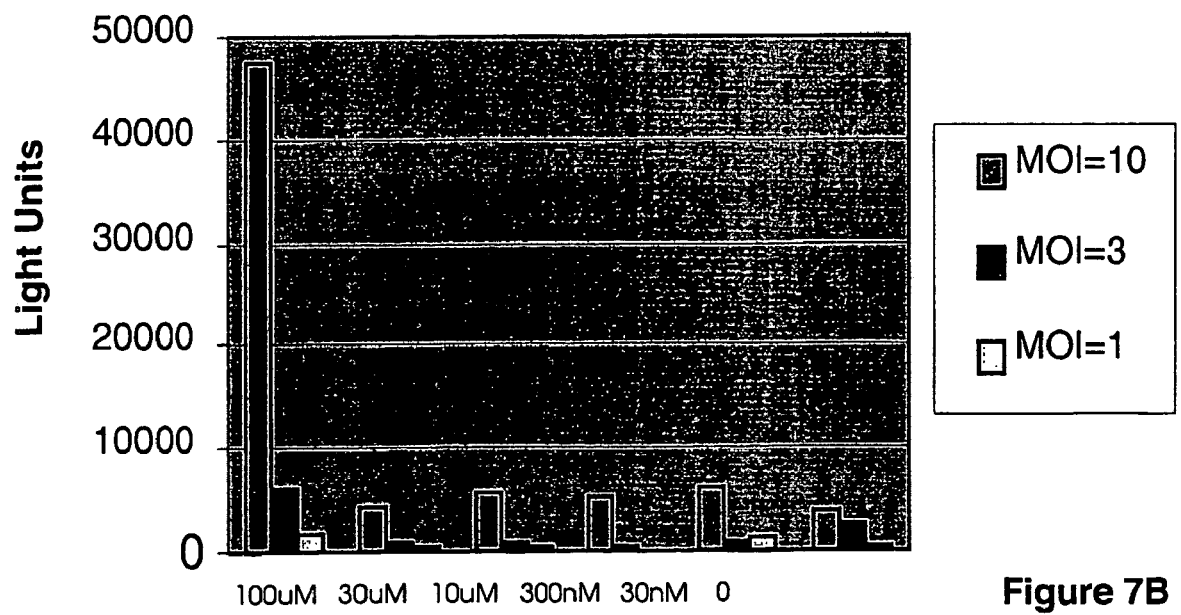
FIG. 7B is a bar graph illustrating luciferase signal in HT29 cells exposed to various concentrations of compound 143491 at differing MOI of an adenovirus vector expressing luciferase.

FIGS. 6A and 6B show a comparison of luciferase expression (y-axis, light units) vs. MOI (x-axis) in HeLa and HT29 cells infected with adenovirus under various conditions. For these studies, cells are grown in 96-well plates. The HT29 cells are seeded at near confluency, about 300,000 cells per well, and infected with adenovirus 3-4 days later. The cells are infected with luciferase-expressing, replication-deficient adenovirus at MOIs of 1, 3 or 10 by applying the virus to wells of cells in low serum medium for 4 hours at 37° C. In addition, the cells are incubated with gene transfer activating compound 143491 at a concentration of 30 nM, 300 nM, 10 uM, 30 uM or 100 uM along with the virus. A control set of cells is incubated with virus at MOIs of 1, 3 or 10, but no gene transfer activating compound is included. Forty-eight hours later, the cells are assayed for luciferase activity by standard techniques. NSC compound 143491 shows activation of adenovirus gene transfer even in HT29 cells. FIGS. 7A and 7B present data from these experiments in which luciferase expression (y-axis, light units) is plotted vs. compound 143491 concentration (x-axis).

Example 13

Figure 8A:
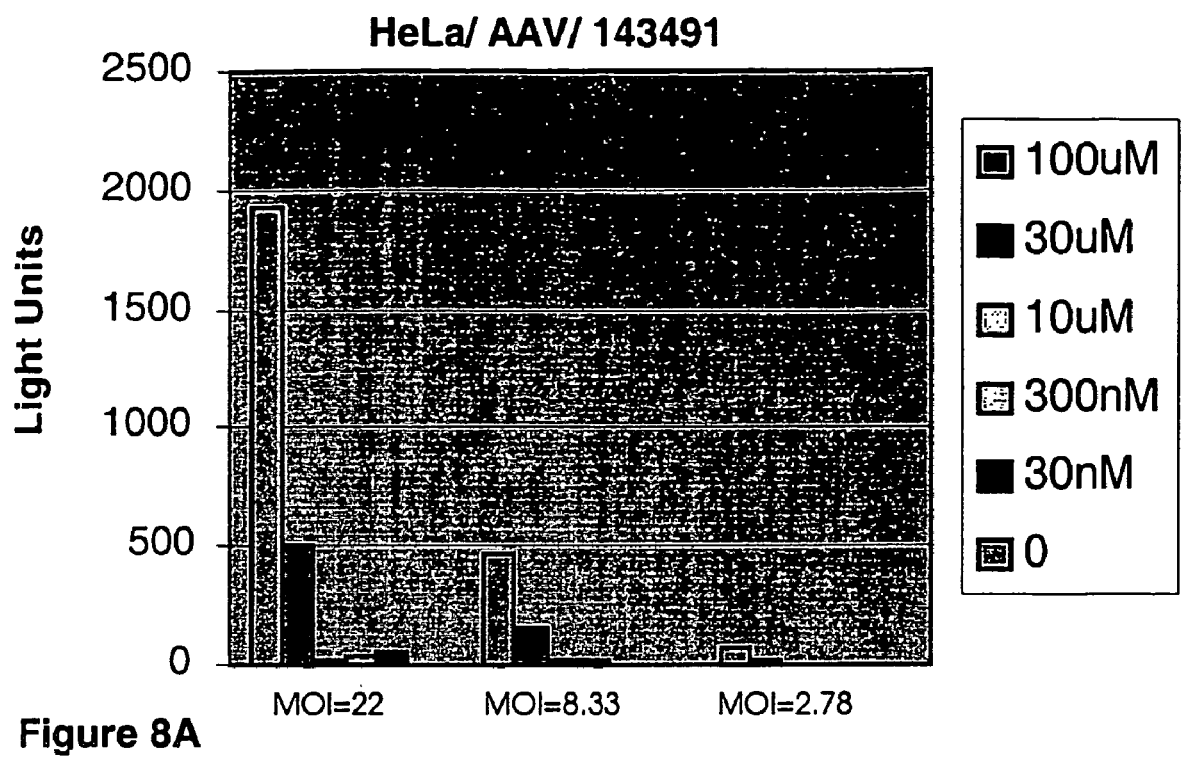
FIG. 8A is a bar graph illustrating luciferase signal in HeLa cells exposed to various concentrations of compound 143491 at differing MOI of an adeno-associated virus vector expressing luciferase.
Figure 8B:
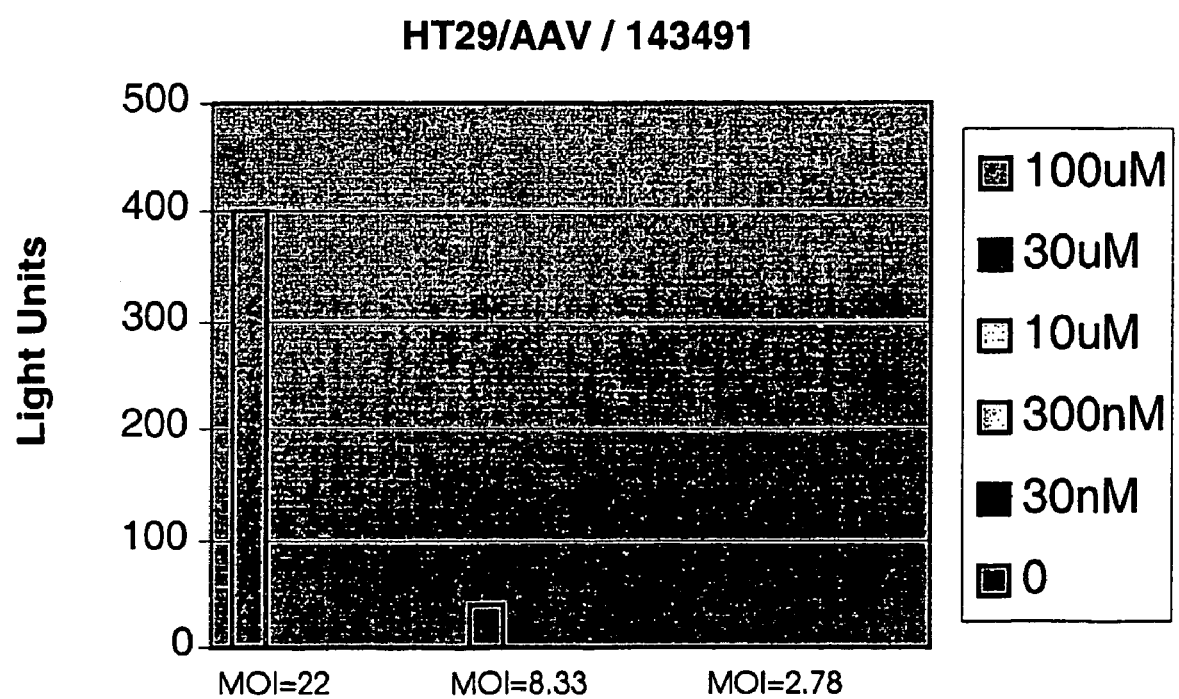
FIG. 8B is a bar graph illustrating luciferase signal in HT29 cells exposed to various concentrations of compound 143491 at differing MOI of an adeno-associated virus vector expressing luciferase.
Figure 9A:
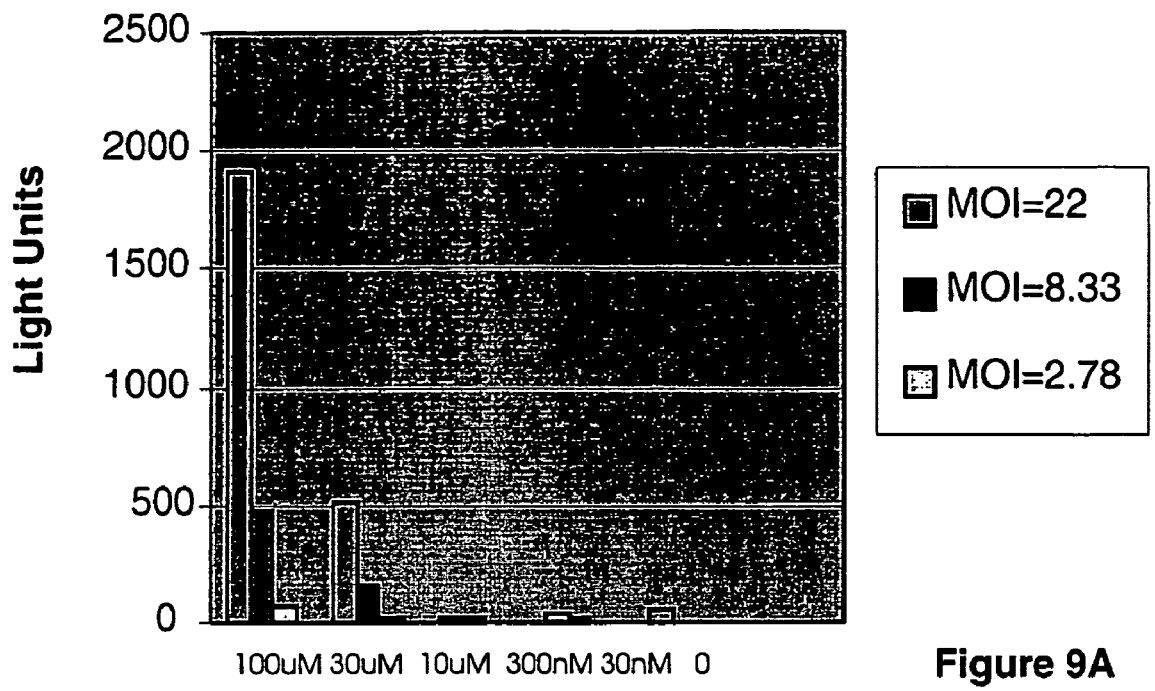
FIG. 9A is a bar graph illustrating luciferase signal in HeLa cells exposed to various concentrations of compound 143491 at differing MOI of an adeno-associated virus vector expressing luciferase.
Figure 9B:
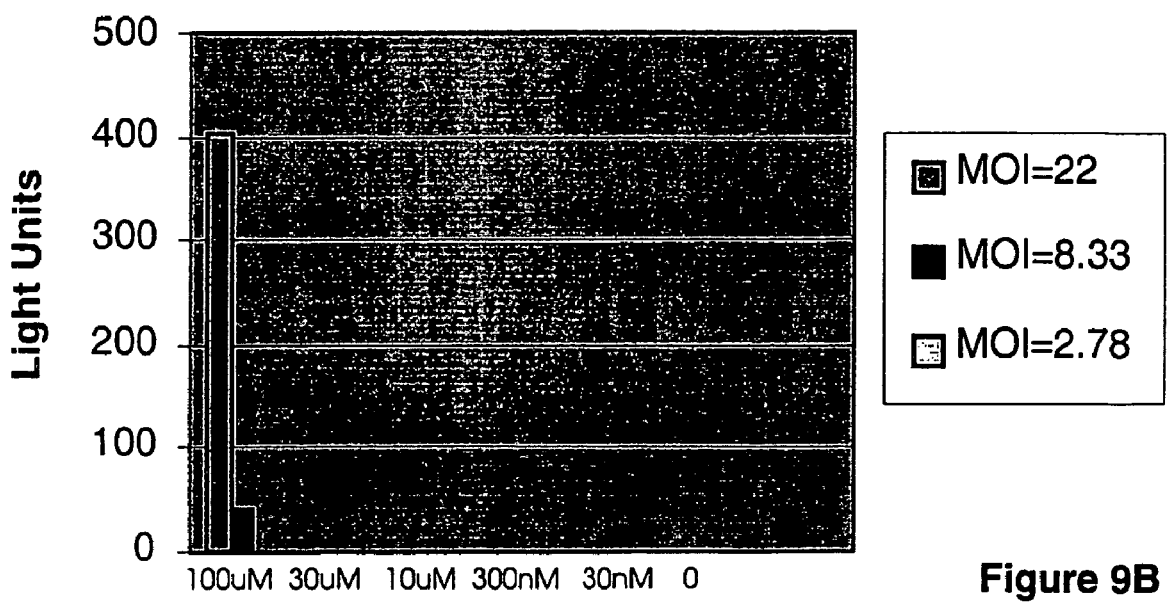
FIG. 9B is a bar graph illustrating luciferase signal in HT29 cells exposed to various concentrations of compound 143491 at differing MOI of an adeno-associated virus vector expressing luciferase.

FIGS. 8A and 8B show a comparison of luciferase expression (y-axis, light units) vs. MOI (x-axis) in HeLa and HT29 cells infected with adeno-associated virus under various conditions. For these studies, cells are grown as described in Example 8. The HT29 cells are seeded at near confluency, about 300,000 cells per well, and infected with adenovirus 3-4 days later. The cells are infected with luciferase-expressing, adeno-associated virus at MOIs of 2.78, 8.33 or 22 by applying the virus to wells of cells in low serum medium for 4 hours at 37° C. In addition, the cells are incubated with gene transfer activating compound 143491 at a concentration of 30 nM, 300 nM, 10 uM, 30 uM or 100 uM along with the virus. A control set of cells is incubated with virus at MOIs of 2.78, 8.33 or 22, but no gene transfer activating compound is included. Forty-eight hours later, the cells are assayed for luciferase activity by standard techniques. Luciferase activity is enhanced in cells treated with compound 143491 compared with controls. FIGS. 9A and 9B present data from these experiments in which luciferase expression (y-axis, light units) is plotted vs. compound 143491 concentration (x-axis).

Example 14

Figure 10:
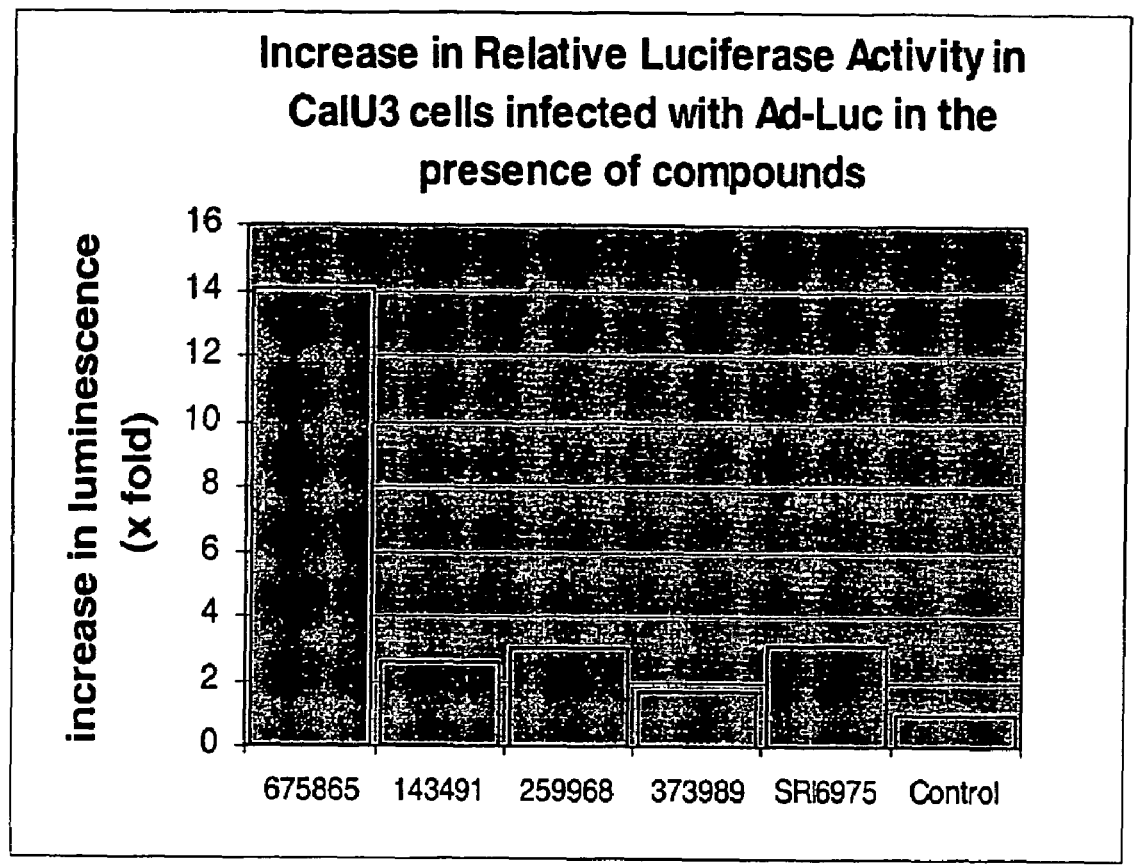
FIG. 10 is a bar graph illustrating fold increase in luminescence signal in Calu3 cells exposed to 40 micromolar of various activating compounds at an MOI of 10 of an adenovirus luciferase expression vector.

Calu3 cells grown as described in Example 9 are incubated with luciferase-expressing adenovirus and various gene transfer activating compounds. FIG. 10 shows the results of these experiments and demonstrates increases in luciferase activity of about 1.5 to 14 fold when cells are infected with adenovirus in the presence of a gene transfer activating compound.

Example 15

In vivo carcinoma models

D54MG tumor cells ($2 \times 10^7$), PC-3 prostate tumor cells ($2 \times 10^7$) or HT29 colonic carcinoma cells ($2 \times 10^7$) are injected subcutaneously into the flanks of nude mice (nu/nu) (e.g. from Taconic Farms). Resulting tumors are measured with calipers approximately two times each week and an estimate of weight (mg) calculated as described in Reference 2. Mice are evaluated for weight loss, tumor mass, and overall appearance every 3 days.

Example 16

Adenovirus construct expressing *E. coli* purine nucleoside phosphorylase

The *E. coli* PNP gene is excised from pSV-PNP (19) using BamHI and inserted into the pACCMVpLpA adenoviral transfer vector. (17). Recombinant adenovirus is constructed by co-transfecting 293 cells in 6-well plates with the plasmid pJM17 (Microbix, Canada) and pACCMVpLpA-PNP (17). Adenoviral DNA is purified from 200 μl of tissue culture supernatant using a kit from Qiagen. PCR-based screening (using viral DNA as template) with PNP specific primers is used to identify recombinant adenovirus, and recombinants are plaque purified by iterative infection of 293 cells with serially diluted viral stocks from single plaques. Functional expression of PNP from recombinant virus is confirmed by HPLC of infected cell lysates. Ad-PNP is prepared by the CsCl gradient centrifugation (18), and replication competent adenovirus (RCA) excluded by a PCR based assay using E1-specific primers that produce products only in the presence of RCA (19). Recombinant adenovirus constructs expressing EGFP (enhanced green fluorescence protein) or luciferase are constructed using an otherwise identical vector backbone using the same or similar techniques.

Example 17

Lentivirus construct expressing *E. coli* purine nucleoside phosphorylase

Lentivirus construction is performed according to the method of Trono et at. (23, 24). In order to establish a lentivirus capable of PNP expression, the gene is PCR amplified using primers 5'ggatccaccatggctaccccacacattaatg 3' (BamHI site and ATG underlined) (SEQUENCE ID No. 1) and 5'cctcgagtcactctttatcgcccagcag 3' (XhoI site underlined) (SEQUENCE ID No. 2). The resulting product is subcloned into Zero-Blunt (Invitrogen). Following digestion with BamHI and XhoI, the PNP gene is cloned to replace the luciferase gene in the pHR'CMYLuc W Sin-18 lentivirus vector. Correct insertion is verified by sequencing the entire PNP gene and the ligation sites, and by transfecting the resulting plasmid (which encodes a CMV promoter driven PNP gene) into 293T cells and verifying the expression of *E. coli* PNP enzymatic activity by HPLC in vitro (see above). The plasmid is then transfected into 293T cells together with two packaging plasmid vectors, pMD.G (envelope) and pCMVDR8.91 (packaging construct). Replication deficient viral particles encoding *E. coli* PNP are collected from tissue culture supernatant following transfection and lentivirus stock concentrated by sucrose cushion centrifugation. The titer of virus stock is estimated by performing parallel EGFP (enhanced green fluorescent protein)-lentivirus production engineered in an otherwise identical vector context using the same procedures, and then by estimating the number of green cells when infected with the EGFP virus stock. The titer of lentivirus reaches $1 \times 10^9$ infectious particles/ml following concentration. A luciferase expressing lentivirus construct is made according to similar procedures.

Example 18

Measurement of *E. coli* PNP activity

Crude cell extracts are prepared from cells transduced with the *E. coli* PNP gene as described (20,21). The extracts are incubated with various concentrations of MeP-dR and the formation of product is measured by HPLC analysis of the reaction mixture. Activity may be expressed as PNP units (22); one unit representing one nmole MeP-dR converted/mg tumor cell extract/hour.

Example 19

Measurement of Luciferase Activity

Luciferase activity is measured using a commercially available assay kit (Bright-Glo™, Promega) designed for high throughput screening. Briefly, the Bright-Glo™ substrate is dissolved in Bright-Glo™ assay buffer at room temperature. 50 µl of the premixed Bright-Glo™ reagent is directly added to each well of the assay plate. Luminescence is measured in a microluminometer (Harta Instrument, Gaithersburg, Md.).

Example 20

Administration of a Gene Expression Enhancement Composition to a Subject

Recombinant virus and a gene transfer activator compound are premixed before administration. The mixture (100 µl, $2-3 \times 10^9$ PFU) is injected intratumorally as described in Example 15 through four needle tracks into a subject having a tumor.

Example 21

Assessment of reporter gene activity in a subject treated with a gene expression enhancement composition Adenovirus expressing PNP (100 µl, $2-3 \times 10^9$ PFU) is injected into mouse PC-3 tumors established as described in Example 15. The adenovirus is mixed before injection with either gene transfer activator compound (final concentration in the mixture of 1 milimolar, in an injection compatible buffer) or an equal volume of the injection compatible buffer. Tumors are removed and assayed for PNP expression as in Example 18. Non-injected tissues, such as liver, are also assayed for PNP expression.

REFERENCES

1. Clancy J P, E J Sorscher. Liposomes for gene transfer. *Gene Therapy Technologies and Regulations: From Laboratory to Clinic*, A. Meager, Ed., 1999.
2. Parker W B, S A King, P W Allan, L L Bennett Jr., J A Secrist III, J A Montgomery, K S Gilbert, W R Waud, A H Wells, G Y Gillespie, E J Sorscher. In vivo gene therapy of cancer with *E. coli* purine nucleoside phosphorylase. *Human Gene Therapy* 8:1637-1644, 1997.
3. Hughes B W, S A King, P W Allan, W B Parker, E J Sorscher. Cell to cell contact is not required for bystander cell killing by *Escherichia coli* purine nucleoside phosphorylase. *J. Bio. Chem.* 273:2322-2328, 1998.
4. Zabner J, P Freimuth, A Puga, A Fabrega, M J Welsh. Lack of high affinity fiber receptor activity explains the resistance of ciliated airway epithelia to adenovirus infection. *J. Clin. Invest.* 100:1144-9, 1997.
5. Grubb B R, R J Pickles, H Ye, J R Yankaskas, R N Vick, J F Engelhardt, J M Wilson, L G Johnson, R C Boucher. Inefficient gene transfer by adenovirus vector to cystic fibrosis airway epithelia of mice and humans. *Nature* 371: 802-806.
6. Goldman M J, J M Wilson. Expression of αvβ integrin is necessary for efficient adenovirus-mediated gene transfer in the human airway. *J. Virology* 69:5951-5958, 1995.
7. Myles C T, M Zhang, J C Kappes, Sorscher E J, Matalon S. Augmentation of adenovirus and lentivirus mediated gene transfer in lungs and epithelial cells by EGTA. *Ped. Pulm. Suppl.* 20:240 (Abst. 240), 2000.
8. Wang G, V Slepushkin, J Zabner, S Keshavjee, J C Johnston, S L Sauter, D J Jolly T W Dubensky, B L Davidson, P B McCray. Feline immunodeficiency virus vectors persistently transduce nondividing airway epithelia and correct the cystic fibrosis defect. *J. Clin. Invest.* 104(11): R55-62, 1999.
9. Ziady A, T Ferkol. DNA condensation and receptor-mediated gene transfer. *Gene Therapy Technologies, Applications and Regulations*. Ed. A. Meager, 1999.

10. Günzburg W H, B Salmons. Retroviral vectors. *Gene Therapy Technologies, Applications and Regulations*. Ed. A. Meager, 1999.
11. Lockett L J, Molloy P L, Russell P J, Both G W. Relative efficiency of tumor cell killing in vitro by two enzyme-prodrug systems delivered by identical adenovirus vectors. *Clin. Cancer Res.* 3:2075-2080, 1997.
12. Zufferery R, T Dull, R J Mandel, A Bukovsky, D Quiroz, L Naldini, D Trono. Self-inactivating lentivirus vector for safe and efficient in vivo gene delivery. *J. Virology* 72(12): 9873-80, 1998.
13. Lashford L S, L J Fairbairn, J E Wraith. Lysosomal storage disorders. *Gene Therapy Technologies, Applications and Regulations*. Ed. A. Meager, 1999.
14. Chamber R, G Y Gillespie, L Soroceanu, S Andreansky, S Chatterjee, J Chou, B Roizman, R J Whitley. Comparison of genetically engineered herpes simplex viruses for treatment of brain tumors in a scid mouse model of human malignant glioma. *Proc. Natl. Acad. Sci USA* 92:1411-1415, 1995.
15. Puhlmann M, M Gant, C K Brown, H R Alexander, D L Bartlett. Thymidine kinase-deleted vaccinia virus expressing purine nucleoside phosphorylase as a vector for tumor directed gene therapy. *Human Gene Therapy* 10:649-657, 1999.
16. Yamamoto K, R Morishita, N Tomita, S Shimozato, H Nakagami, A Kikuchi, M Aoki, J Higaki, Y Kaneda, T Ogihara. Ribozyme oligonucleotides against transforming growth factor-beta inhibited neointimal formation after vascular injury in rat model: Potential application of ribozyme strategy to treat cardiovascular disease. *Circulation* 102(11):1308-14, 2000.
17. Becker, T. C., et al., Use of recombinant adenovirus for metabolic engineering of mammalian cells, In Methods in Cell Biology, 1994, Academic Press, p.161-189.
18. Wold, W. S. M., Ed. Adenovirus Methods and Protocols. Methods in Molecular Medicine. 1999. Humana Press, Totowa, N.J.
19. Jensen, K. F. and Nygaard, P. 1975. Purine nucleoside phosphorylase from *Escherichia coli* and *Salmonella typhimurium*. Purification and some properties. Eur. J. Biochem. 51:253-265.
20. Sorscher, E. J. et al., (1994), Tumor cell bystander killing in colonic carcinoma utilizing the *E. coli* Deo D gene and generation of toxic purines. *Gene Therapy* 1, 233-238.
21. Parker W. B., et al. (1997) In vivo gene therapy of cancer with *E. coli* purine nucleoside phosphorylase. Human Gene Therapy 8:1637-1644.
22. Gadi V. K., et al., (2000) In vivo sensitization of ovarian tumors to chemotherapy by expression of *E. coli* purine nucleoside phosphorylase in a small fraction of tumor cells. Gene Therapy 7: 1738-1743.
23. Zufferey, R., D. Nagy, R. J. Mandel, L. Naldini, and D. Trono. 1997. Multiply attenuated lentiviral vector achieves efficient gene delivery in vivo. Nat. Biotechnol. 15:871-875.
24. Zufferey R, Dull T, Mandel R J, Bukovsky A, Quiroz D, Naldini L, Trono D Self-inactivating lentivirus vector for safe and efficient in vivo gene delivery. J. Virol. 1998 December; 72(12):9873-80.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

The invention claimed is:

1. A kit for activating gene transfer, said kit comprising a gene transfer activating compound packaged in a suitable container together with instructions for use to activate gene transfer wherein said gene transfer compound is selected from the group consisting of:

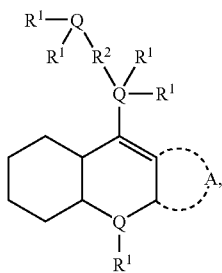

(I)

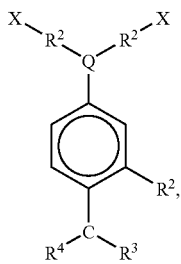

(II)

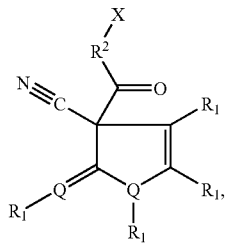

(III)

$R^2$—$AsO_3H_2$, (IV)

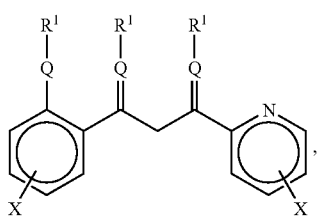

(V)

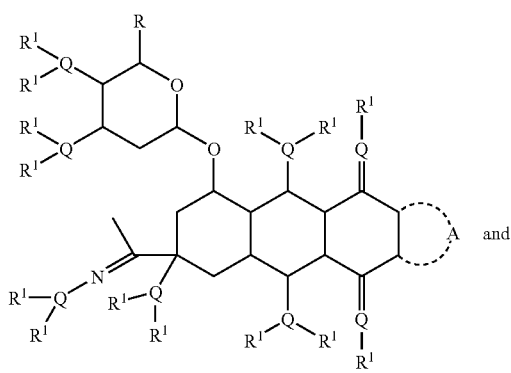

and (VI)

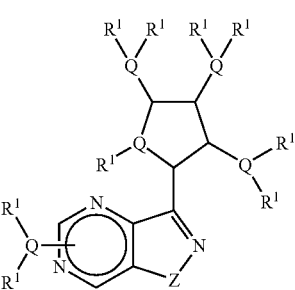

(VII)

wherein Q is nitrogen or oxygen, wherein each occurrence of $R^1$ independently is H, $CH_3$, $CH_2CH_3$ or a nullity, wherein $R^2$ is $C_1$-$C_{18}$ alleyl, $C_2$-$C_{18}$ ether, $C_2$-$C_{18}$ thioether, $C_2$-$C_{18}$ secondary or tertiary amine, wherein A is

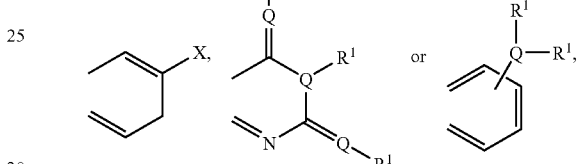

wherein $R^3$ is H, $C_1$-$C_6$ alkyl, or a heteroatom substituted $C_1$-$C_6$ alkyl where the heteroatom is oxygen, nitrogen, or sulfur, wherein $R^4$ is $C_2$-$C_6$ amide; or =N—$R^5$ where $R^5$ is $C_7$-$C_{12}$ aryloxyl, $C_1$-$C_6$ hydronyl, carbonyl, carboxyl, or acyl, imidazyl, pyrazyl, thiazyl, or oxazyl, wherein X is H, F, Cl or Br, wherein Z is oxygen or sulfur.

2. The kit of claim 1 wherein said gene transfer compound is bouvardin.

3. The kit of claim 1 wherein said gene transfer compound is that of structure I, wherein A is

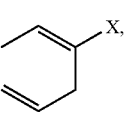

and Q is nitrogen in each occurrence.

4. The kit of claim 1 wherein said gene transfer compound is that of structure I, wherein A and each occurrence of Q together are

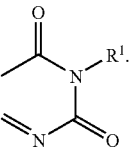

5. The kit of claim 1 wherein said gene transfer compound is that of structure II wherein Q is nitrogen and $R^2$ is $C_1$-$C_{18}$ alkyl.

6. The kit of claim 5 wherein $R^4$ is =N—$R^5$.

7. The kit of claim 5 wherein X is Cl or Br.

8. The kit of claim 1 wherein said gene transfer compound is that of structure III wherein Q in each occurrence together are

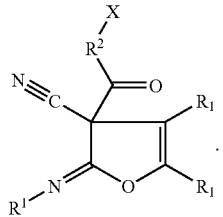

9. The kit of claim 8 wherein said gene transfer compound is that of structure II or VII wherein each occurrence of $R^1$ is H, or $CH_3$.

10. The kit of claim 1 wherein said gene transfer compound is that of structure V wherein Q in each occurrence is oxygen.

11. The kit of claim 1 wherein said gene transfer compound is that of structure VI wherein Q in each occurrence is oxygen.

12. The kit of claim 11 wherein A is

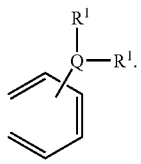

13. The kit of claim 1 wherein said gene transfer compound is that of structure VII wherein Q in each non-aromatic substituent occurrence is oxygen.

14. The kit of claim 13 wherein $R^1$ in each occurrence is H.

15. The kit of claim 1 wherein said compound is selected from the group consisting of:
- 1-(5-chloro-2-hydroxyphenyl)-3-(3-pyridinyl)-1,3propanedione;
- N-(4-(bis(2-chloroethyl)amino)benzylidene)-1,3-thiazol-2-amine;
- 2-((4-(bis(2-chloroethyl)amino)benzylidene)amino)benzoic acid;
- 2-((4-(bis(2-chloroethyl)amino)-2-methylbenzylidene)amino)ethanol;
- 1-Tetradecylarsonic acid;
- 4-(4-(bis(2-chloroethyl)amino)phenyl)-N,N-dimethylbutanamide;
- $N^1$-(2-fluoro-9-acridinyl)-$N^3$,$N^3$-dimethyl-1,3-propanediamine;
- 3-(bromoacetyl)-2-imino-4,5-dimethyl-2,3-dihydro-3-furancarbonitrile;
- 3,5,12-trihydroxy-3-(N-hydroxyethanimidoyl)-10-methoxy-6,11-dioxo-1,2,3,4,6,11-hexahydro-1-naphthacenyl 3-amino-2,3,6-trideoxyhexopyranoside;
- bouvardin;
- 5-((3-(dimethylamino)propyl)amino)-3,10-dimethylpyrimido[4,5-b]quinoline-2,4(3H,10H)-diane; and
- 1-(7-aminoisothiazolo[4,5-d]pyrimidin-3-yl)-1,4-anhydrapentitol.

16. A process for activating gene transfer of a vector to a cell comprising the steps of:
contacting a cell with a recombinant gene transfer vector; and
administering a gene transfer activating compound to the cell, such that transfer of the vector to the cell is activated;
wherein the gene transfer activating compound is selected from the group consisting of:

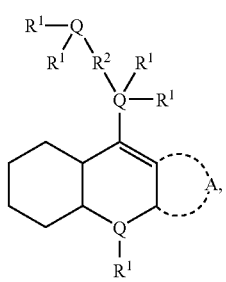
(I)

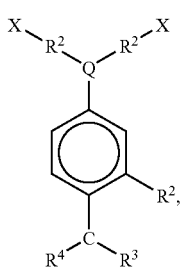
(II)

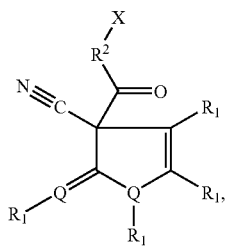
(III)

$R^2$—$AsO_3H_2$, (IV)

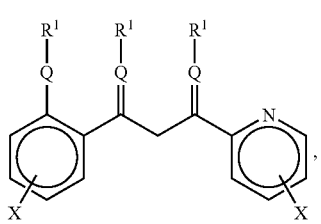
(V)

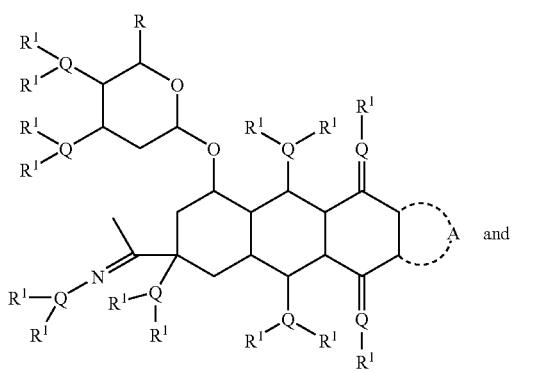
(VI)
and

-continued

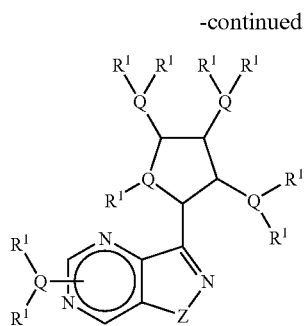
(VII)

wherein Q is nitrogen or oxygen, wherein each occurrence of $R^1$ independently is H, $CH_3$ $CH_2CH_3$ or a nullity, wherein $R^2$ is $C_1$-$C_{18}$ alleyl, $C_2$-$C_{18}$ ether, $C_2$-$C_{18}$ thioether, $C_2$-$C_{18}$ secondary or tertiary amine, wherein A is

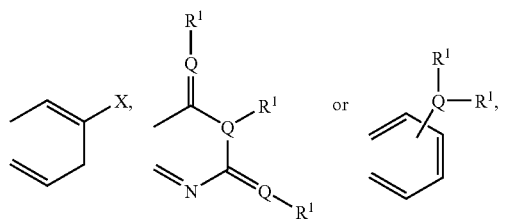

wherein $R^3$ is H, $C_1$-$C_6$ alkyl, or a heteroatom substituted $C_1$-$C_6$ alkyl where the heteroatom is oxygen, nitrogen, or sulfur, wherein $R^4$ is $C_2$-$C_6$ amide, or =N—$R^5$ where $R^5$ is $C_7$-$C_{12}$ aryloxyl, $C_1$-$C_6$ hydronyl, carbonyl, carboxyl, or acyl, imidazyl, pyrazyl, thiazyl, or oxazyl, wherein X is H, F, Cl or Br, wherein Z is oxygen or sulfur.

17. A process for activating gene transfer of a vector to a cell comprising the steps of:
   contacting a cell with a recombinant gene transfer vector; and
   administering a gene transfer activating compound to the cell, such that transfer of the vector to the cell is activated;
   wherein the gene transfer activating compound is selected from the group consisting of:
   1-(5-chloro-2-hydroxyphenyl)-3-(3-pyridinyl)-1,3-propanedione;
   N4(bis(2-chloroethy)amino)benzylidene)1,3-thiazol-2-amine;
   2-((4-(bis(2-chloroethyl)amino)benzylidene)amino)benzoic acid;
   2-((4-(bis(2-chloroethyl)amino)2-methylbenzylidene) amino)ethanol;
   1-Tetradecylarsonic acid;
   4-(4-(bis(2-chloroethyl)amino)phenyl)-N,N-dimethylbutananide;
   $N^1$-(2-fluoro-9-acridinyl)-$N^3N^3$-dimethyl-1,3-propanediamine;
   3-(bromoacetyl)-2-imino-4,5-dimethyl-2,3-dihydro-3-furancarbonitrile;
   3,5,12-trihydroxy-3-(N-hydroxyethanimidoyl)-10-methoxy-6,11-dioxo-1,2,3,4,6,11-hexahydro-1-naphthacenyl 3-amino-2,3,6-trideoxyhexopyranoside;
   bouvardin:
   5-((3-(dimethylamino)propyl)amino)-3,10-dimethylpyrimido[4,5-b]quinoline-2,4(3H,10H)-dione; and
   1-(7-aminoisothiazolo[4,5-d]pyrimidin-3-yl)-1,4-anhydropentitol.

18. A process for determining the efficacy of a putative gene transfer activating compound to activate gene transfer, comprising the steps of:
   administering a test compound to a first cell;
   contacting the first cell with a first amount of a recombinant vector;
   contacting a second cell with a second amount of the recombinant vector, the second amount of the recombinant vector substantially equal to the first amount;
   measuring a gene transfer indicator in the first cell to obtain a test measurement;
   measuring the gene transfer indicator in the second cell to obtain a control measurement; and
   comparing the test measurement and the control measurement to determine the efficacy of the putative gene transfer activating compound to activate gene transfer;
   wherein said acne transfer compound is selected from the group consisting of:

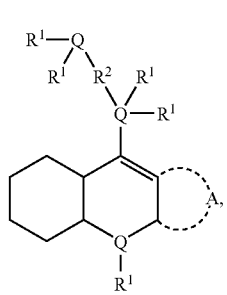
(I)

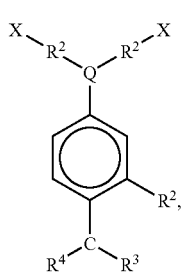
(II)

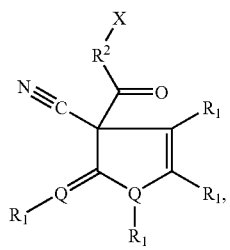
(III)

$R^2$—$AsO_3H_2$,
(IV)

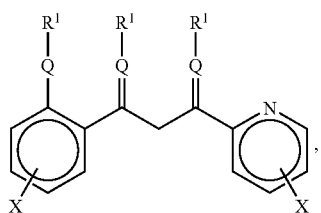
(V)

-continued (VI)

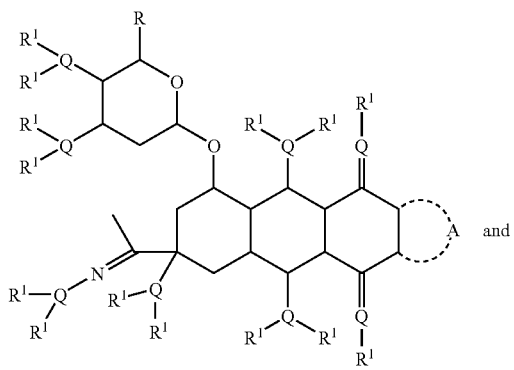

(VII)

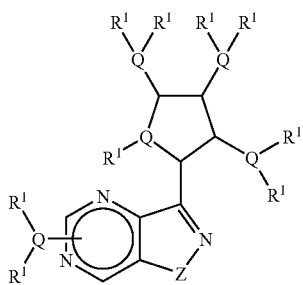

wherein Q is nitrogen or oxygen, wherein each occurrence of $R^1$ independently is H, $CH_3$, $CH_2CH_3$ or a nullity, wherein $R^2$ is $C_1$-$C_{18}$ allyl, $C_2$-$C_{18}$ ether, $C_2$-$C_{18}$ thioether, $C_2$-$C_{18}$ secondary or tertiary amine, wherein A is

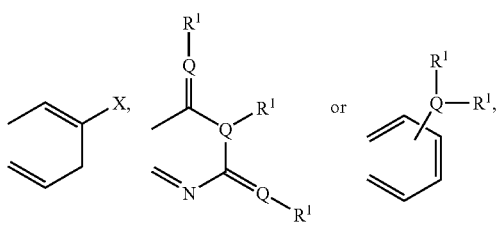

wherein $R^3$ is H, $C_1$-$C_6$ alkyl, or a heteroatom substituted $C_1$-$C_6$ alkyl where the heteroatom is oxygen, nitrogen, or sulfur, wherein $R^4$ is $C_2$-$C_6$ amide, or $=N-R^5$ where $R^5$ is $C_7$-$C_{12}$ aryloxyl, $C_1$-$C_6$ hydronyl, carbonyl, carboxyl, or acyl imidazyl, pyrazyl, thiazyl, or oxazyl, wherein X is H, F, Cl or Br, wherein Z is oxygen or sulfur.

19. The process of claim 18 wherein said gene transfer compound is bouvardin.

20. The process of claim 18 wherein said gene transfer compound is that of structure I, wherein A is

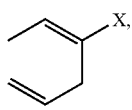

and Q is nitrogen in each occurrence.

21. The process of claim 18 wherein said gene transfer compound is that of structure I, wherein A and each occurrence of Q together are

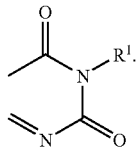

22. The process of claim 18 wherein said gene transfer compound is that of structure II wherein Q is nitrogen and $R^2$ is $C_1$-$C_{18}$ alkyl.

23. The process of claim 18 wherein $R^4$ is $=N-R^5$.

24. The process of claim 18 wherein X is Cl or Br.

25. The process of claim 18 wherein said gene transfer compound is that of structure III wherein Q in each occurrence together are

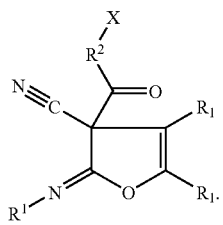

26. The process of claim 18 wherein said gene transfer compound is that of structure II or VII wherein each occurrence of $R^1$ is H, or $CH_3$.

27. The process of claim 18 wherein said gene transfer compound is that of structure V wherein Q in each occurrence is oxygen.

28. The process of claim 18 wherein said gene transfer compound is that of structure VI wherein Q in each occurrence is oxygen.

29. The process of claim 18 wherein A is

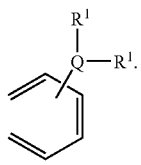

30. The process of claim 18 wherein said gene transfer compound is that of structure VII wherein Q in each non-aromatic substituent occurrence is oxygen.

31. The process of claim 18 wherein $R^1$ in each occurrence is H.

32. The process of claim 18 wherein said compound is selected from the group consisting of:
1-(5-chloro-2-hydroxyphenyl)-3-(3-pyridinyl)-1,3-propanedione;
N-(4-(bis(2-chloroethyl)amino)benzylidene)-1,3-thiazol-2-amine;

2-((4-(bis(2-chloroethyl)amino)benzylidene)amino)benzoic acid;
2-((4-(bis(2-chloroethyl)amino)-2-methylbenzylidene)amino)ethanol;
1-Tetradecylarsonic acid;
4-(4bis(2-chloroethyl)amino)phenyl)-N,N-dimethylbutanamide;
$N^1$-(2-fluoro-9-acridinyl)-$N^3$, $N^3$-dimethyl-1,3-propanediamine;
3-(bromoacetyl)-2-imino-4,5-dimethyl-2,3-dihydro-3-furancarbonitrile;
3,5,12-trihydroxy-3-(N-hydroxyethanimidoyl)-10-methoxy-6,11-dioxo-1,2,3,4,6,11-hexahydro-1-naphthacenyl 3-amino-2,3,6-trideoxyhexopyranoside;
bouvardin;
5-((3-(dimethylamino)propyl)amino)-3,10-dimethylpyrimido[4,5-b]quinoline-2,4(3H,10H)-dione; and 1-(7-aminoisothiazolo[4,5-d]pyrimidin-3-yl)-1,4-anhyciropentitol.

* * * * *

SEQUENCE LISTING

```
<160> NUMBER OF SEQ ID NOS: 2

<210> SEQ ID NO 1
<211> LENGTH: 31
<212> TYPE: DNA
<213> ORGANISM: Artificial
<220> FEATURE:
<223> OTHER INFORMATION: primer for lentivirus construct

<400> SEQUENCE: 1
ggatccacca tggctacccc acacattaat g                           31

<210> SEQ ID NO 2
<211> LENGTH: 28
<212> TYPE: DNA
<213> ORGANISM: Artificial
<220> FEATURE:
<223> OTHER INFORMATION: primer for lentivirus construct

<400> SEQUENCE: 2
cctcgagtca ctctttatcg cccagcag                              28
```